United States Patent
Langham et al.

(10) Patent No.: US 6,740,654 B2
(45) Date of Patent: *May 25, 2004

(54) SQUARIC ACID DERIVATIVES

(75) Inventors: Barry John Langham, Reading (GB); Rikki Peter Alexander, High Wycombe (GB); John Clifford Head, Maidenhead (GB); Janeen Marsha Linsley, High Wycombe (GB); John Robert Porter, Chinnor (GB); Sarah Catherine Archibald, Maidenhead (GB); Graham John Warrellow, Northwood (GB)

(73) Assignee: Celltech R & D Limited, Berkshire (GB)

( * ) Notice: Subject to any disclaimer, the term of this patent is extended or adjusted under 35 U.S.C. 154(b) by 0 days.

This patent is subject to a terminal disclaimer.

(21) Appl. No.: 09/899,488

(22) Filed: Jul. 5, 2001

(65) Prior Publication Data

US 2002/0107263 A1 Aug. 8, 2002

(30) Foreign Application Priority Data

Jul. 7, 2000 (GB) .............................................. 0016785
Nov. 21, 2000 (GB) .............................................. 0028364

(51) Int. Cl.[7] ................... C07D 235/14; C07D 495/04; A61K 31/4184; A61K 31/519; A61P 19/02

(52) U.S. Cl. ....................... 514/243; 514/246; 514/249; 514/250; 514/258.1; 514/259.1; 514/259.2; 514/259.3; 514/259.31; 514/259.4; 514/260.1; 514/261.1; 514/262.1; 514/263.1; 514/264.1; 514/265.1; 514/266.1; 514/300; 514/301; 514/302; 514/303; 514/305; 514/306; 514/307; 514/311; 514/367; 514/375; 514/379; 514/394; 514/403; 514/412; 514/415; 544/182; 544/183; 544/184; 544/235; 544/236; 544/237; 544/257; 544/258; 544/262; 544/263; 544/277; 544/278; 544/279; 544/280

(58) Field of Search ................................. 514/243, 246, 514/248, 250, 258.1, 259.1, 259.2, 259.3, 259.31, 259.4, 260.1, 261.1, 262.1, 263.1, 264.1, 265.1, 266.1, 300, 301, 302, 303, 305, 306, 307, 311, 367, 375, 379, 394, 403, 412, 415, 182, 183, 184, 235, 236, 237, 257, 258, 262, 263, 277, 278, 279, 280, 281, 282, 283; 546/113, 114, 115, 118, 119, 121, 122, 133, 138, 146, 174; 548/180, 217, 241, 309.7, 362.5, 453, 503

(56) References Cited

U.S. PATENT DOCUMENTS

| | | | |
|---|---|---|---|
| 4,470,973 A | 9/1984 | Natarajan et al. | ............ 424/177 |
| 4,554,273 A | 11/1985 | Bayssat et al. | .............. 514/221 |
| 4,987,132 A | 1/1991 | Mase et al. | .................. 514/252 |
| 5,164,372 A | 11/1992 | Matsuo et al. | ................. 514/19 |
| 5,227,490 A | 7/1993 | Hartman et al. | ............. 514/317 |

(List continued on next page.)

FOREIGN PATENT DOCUMENTS

| | | |
|---|---|---|
| DE | 23 16 881 A | 10/1973 |
| DE | 28 37 264 A1 | 3/1979 |

(List continued on next page.)

OTHER PUBLICATIONS

Wermuth, C.G., in "The Practice of Medicinal Chemistry", 1996, Academic Press, pp. 215–217.*

(List continued on next page.)

Primary Examiner—Mukund J. Shah
Assistant Examiner—Thomas McKenzie
(74) Attorney, Agent, or Firm—Woodcock Washburn LLP

(57) ABSTRACT

Squaric acid derivatives of formula (1) are described:

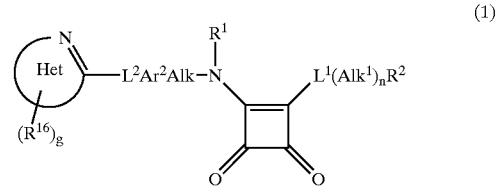

wherein
Het is an optionally substituted bicyclic fused ring heteroaromatic group;
$L^2$ is a covalent bond or an atom or group —O—, —S—, —C(O)—, —C(S)—, —S(O)—, —S(O)$_2$—, —N(R$^8$)— or —C(R$^8$)(R$^{8a}$)—;
$Ar^2$ is an optionally substituted aromatic or heteroaromatic group;
Alk is a chain

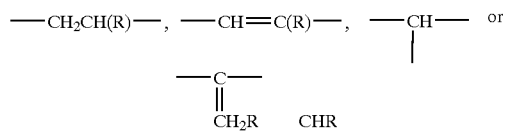

in which R is a carboxylic acid (—CO$_2$H) or a derivative or biostere thereof;
$R^1$ is a hydrogen atom or a $C_{1-6}$alkyl group;
$L^1$ is a covalent bond or a linker atom or group;
$Alk^1$ is an optionally substituted aliphatic chain;
n is zero or the integer 1;
$R^2$ is a hydrogen atom or an optionally substituted heteroaliphatic, cycloaliphatic, heterocycloaliphatic, polycycloalphatic, heteropolycycloaliphatic, aromatic or heteroaromatic group other than a 2,6-naphthyridin-1-yl, isoquinolin-1-yl, 2,7-naphthyridin-1-yl or quinazolin-4-yl group;
and the salts, solvates, hydrates and N-oxides thereof.

The compounds are able to inhibit the binding of integrins to their ligands and are of use in the prophylaxis and treatment of immune or inflammatory disorders, or disorders involving the inappropriate growth or migration of cells.

24 Claims, No Drawings

U.S. PATENT DOCUMENTS

| | | | |
|---|---|---|---|
| 5,260,277 A | 11/1993 | McKenzie | 544/18 |
| 5,296,486 A | 3/1994 | Lazer et al. | 514/333 |
| 5,399,585 A | 3/1995 | Alig et al. | 514/438 |
| 5,510,346 A | 4/1996 | Martin et al. | 514/221 |
| 5,698,691 A | 12/1997 | Yukimasa et al. | 540/490 |
| 5,773,646 A | 6/1998 | Chandra Kumar et al. | 562/439 |
| 6,093,696 A | 7/2000 | Head et al. | 514/19 |
| 6,110,945 A | 8/2000 | Head et al. | 514/332 |
| 6,166,050 A | 12/2000 | Lembardo et al. | 514/352.18 |
| 6,197,794 B1 | 3/2001 | Head et al. | 514/342 |
| 6,211,220 B1 * | 4/2001 | Pamukcu et al. | 514/247 |
| 6,274,577 B1 | 8/2001 | Brown et al. | 514/221 |
| 6,329,362 B1 | 12/2001 | Archibald et al. | 514/188 |
| 6,329,372 B1 | 12/2001 | Head et al. | 514/241 |
| 6,348,436 B1 | 2/2002 | Langlois et al. | 507/112 |
| 6,362,204 B1 | 3/2002 | Head et al. | 514/342 |
| 6,369,229 B1 | 4/2002 | Head et al. | 546/264 |
| 6,403,608 B1 | 6/2002 | Langham et al. | 514/309 |
| 6,455,539 B2 * | 9/2002 | Langham et al. | 514/300 |
| 6,465,471 B1 | 10/2002 | Warrellow et al. | 514/256 |
| 6,469,025 B1 | 10/2002 | Head et al. | 514/307 |
| 6,518,283 B1 * | 2/2003 | Langham et al. | 514/317 |

FOREIGN PATENT DOCUMENTS

| | | |
|---|---|---|
| DE | 196 54 483 A | 1/1998 |
| EP | 0 031 104 A1 | 7/1981 |
| EP | 0 048 763 A1 | 4/1982 |
| EP | 0 144 230 A2 | 6/1985 |
| EP | 0 288 176 A1 | 10/1988 |
| EP | 0 322 068 A1 | 6/1989 |
| EP | 0 394 989 A2 | 10/1990 |
| EP | 0 498 268 A2 | 8/1992 |
| EP | 0 596 406 A1 | 5/1994 |
| EP | 0 710 657 A1 | 5/1996 |
| EP | 0 710 659 A1 | 5/1996 |
| EP | 0 842 943 A2 | 5/1998 |
| EP | 0 842 945 A2 | 5/1998 |
| JP | 56 090045 | 7/1981 |
| JP | 03 135962 | 6/1991 |
| WO | WO 86/02353 | 4/1986 |
| WO | WO 93/00095 | 1/1993 |
| WO | WO 93/08174 | 4/1993 |
| WO | WO 93/09795 | 5/1993 |
| WO | WO 94/15954 | 7/1994 |
| WO | WO 94/15955 | 7/1994 |
| WO | WO 94/29277 A1 * | 12/1994 |
| WO | WO 94/29285 | 12/1994 |
| WO | WO 95/13811 | 5/1995 |
| WO | WO 95/15973 | 6/1995 |
| WO | WO 95/19356 | 7/1995 |
| WO | WO 95/35314 | 12/1995 |
| WO | WO 96/01644 | 1/1996 |
| WO | WO 96/22966 | 8/1996 |
| WO | WO 96/26190 | 8/1996 |
| WO | WO 97/03094 | 1/1997 |
| WO | WO 97/04247 | 2/1997 |
| WO | WO 97/08145 | 3/1997 |
| WO | WO 97/12866 | 4/1997 |
| WO | WO 97/23480 | 7/1997 |
| WO | WO 97/24124 | 7/1997 |
| WO | WO 97/31907 | 9/1997 |
| WO | WO 97/36858 | 10/1997 |
| WO | WO 97/36859 | 10/1997 |
| WO | WO 97/36861 | 10/1997 |
| WO | WO 97/36862 | 10/1997 |
| WO | WO 97/44333 | 11/1997 |
| WO | WO 97/47618 | 12/1997 |
| WO | WO 98/00395 | 1/1998 |
| WO | WO 98/04247 | 2/1998 |
| WO | WO 98/04913 | 2/1998 |
| WO | WO 98/18460 | 5/1998 |
| WO | WO 98/25892 | 6/1998 |
| WO | WO 98/31359 | 7/1998 |
| WO | WO 98/42662 | 10/1998 |
| WO | WO 98/53814 | 12/1998 |
| WO | WO 98/53817 | 12/1998 |
| WO | WO 98/53818 | 12/1998 |
| WO | WO 98/54207 | 12/1998 |
| WO | WO 98/58902 | 12/1998 |
| WO | WO 99/06390 | 2/1999 |
| WO | WO 99/06431 | 2/1999 |
| WO | WO 99/06432 | 2/1999 |
| WO | WO 99/06433 | 2/1999 |
| WO | WO 99/06434 | 2/1999 |
| WO | WO 99/06435 | 2/1999 |
| WO | WO 99/06436 | 2/1999 |
| WO | WO 99/06437 | 2/1999 |
| WO | WO 99/10312 | 3/1999 |
| WO | WO 99/10313 | 3/1999 |
| WO | WO 99/20272 | 4/1999 |
| WO | WO 99/26921 | 6/1999 |
| WO | WO 99/26922 | 6/1999 |
| WO | WO 99/26945 | 6/1999 |
| WO | WO 99/30709 | 6/1999 |
| WO | WO 99/31061 | 6/1999 |
| WO | WO 99/31099 | 6/1999 |
| WO | WO 99/32457 | 7/1999 |
| WO | WO 99/35163 | 7/1999 |
| WO | WO 99/36393 | 7/1999 |
| WO | WO 99/37618 | 7/1999 |
| WO | WO 99/43642 | 9/1999 |
| WO | WO 99/44994 | 9/1999 |
| WO | WO 99/48879 | 9/1999 |
| WO | WO 99/52879 | 10/1999 |
| WO | WO 99/52896 | 10/1999 |
| WO | WO 99/52898 | 10/1999 |
| WO | WO 99/60015 | 11/1999 |
| WO | WO 99/61465 | 12/1999 |
| WO | WO 99/64395 | 12/1999 |
| WO | WO 99/67230 | 12/1999 |
| WO | WO 00/00486 | 1/2000 |
| WO | WO 00/01383 | 1/2000 |
| WO | WO 00/06169 | 2/2000 |
| WO | WO 00/07544 | 2/2000 |
| WO | WO 00/17197 | 3/2000 |
| WO | WO 00/23419 | 4/2000 |
| WO | WO 00/31067 | 6/2000 |
| WO | WO 00/35855 | 6/2000 |
| WO | WO 00/73260 | 12/2000 |
| WO | WO 01/47867 A1 | 7/2001 |

OTHER PUBLICATIONS

West, Anthony R., Solid State Chemistry and its Applications, Wiley, New York, 1988, pp. 358 & 365.*

Polman, C.H. et al, BMJ 2000, 321, 490–4.*

Cohen, J.A. et al, J. Neuroimmun., 1999, 98 29–36.*

Merriam–Webster Collegiate Dictionary, 10ed., no author listed, 1998, p. 288.*

Abraham, W.M. et al., "$\alpha_4$–Integrins Mediate Antigen–Induced Late Bronchial Responses and Prolonged Airway Hyperresponsiveness in Sheep," *J. Clin. Invest.*, 1994, 93, 776–787.

Alhaique, F., et al., "Cyclisation of dinitriles by sodium alkoxides a new synthesis of naphthyridines," *Tetrahedron Letters*, 1975, 3, 173–174.

Ames, D.E., et al., "Condensation of β–dicarbonyl compounds with halogenopyridinecarb–oxylic acids. A convenient synthesis of some naphthyridine derivatives," *J.C.S. Perkin I,* 1972, 705–710.

Azzouny, A.E., et al., "Zur Synthese Acyclischer und Cyclischer Anthranilsäure–Phenylalanin–Peptide," *Pharmazie,* 1977, 32(6), 318–323 (German language only).

Bach et al., "Anomalous optical rotation and circular dichroism of N–thioacylated alpha amino acids and deriva," *Acta Chem. Scand.,* 1966, 20(10), 2781–2794.

Badshah, A., et al., "Catalytic reduction of azlactones in alkaline media. Synthesis of amino acids," *J. of Organic Chemistry,* 1972, 37(18), 2916–2918.

Barrett, G.C., "Circular dichroism of N–thiobenzoly–1–α–amino acids. III. Their circular dichroism through the near–ultraviolet wavelength range," *J. Chem. Soc.,* 1967, Section C, 1–5.

Berlin, C. et al., "α4β7 Integrin Mediates Lymphocyte Binding to the Mucosal Vascular Addressin MAdCAM–1," *Cell,* 1993, 74, 185–195.

Binns, R.M. et al., "The Role of E–Selectin in Lymphocyte and Polymorphonuclear Cell Recruitment into Cutaneous Delayed Hypersensitivity Reactions in Sensitized Pigs," *J. Immunol.,* 1996, 157, 4094–409.

Bodor, N., "Novel approaches in prodrug design," *Alfred Benzon Symposium,* 1982, 17, 156–177.

Briskin, M.J. et al., "Structural Requirements for Mucosal Vascular Addressin Binding to Its Lymphocyte Receptor $\alpha_4\beta_7$," *J. Immunol.,* 1996, 156, 719–726.

Brooks, Peter C., et al., "Antiintegrin αvβ3 blocks human breast cancer growth and angiogenesis in human skin," *J. Clin. Invest.,* 1995, 96, 1815–1822.

Buckle, D.R., et al., "Non Thiazolidinedione Antihyperglycaemic Agents. 1: α–Heteroatom Substituted β–Phenylpropanoic Acids," *Bioorg. Med. Chem. Lett.,* 1996, 6(17), 2121–2126.

Cardarelli, P.M. et al., "Cyclic RGD Peptide Inhibits α4β7 Interaction with Connecting Segment 1 and Vascular Cell Adhesion Molecule," *J. Biol. Chem.,* 1994, 269(28), 18668–18673.

"Cephalosporins," *Jpn. Kokai Tokkyo Koho,* 40 pages, doc. No. 99:5433 (abstract only, 2 pages); JP 57118588.

Koho, *Chemical Abstracts,* "N–[4–Thiazolidinyl)carbonyl] amino acid derivatives," 1981, 95(19), Abstract No. 169173f, 1 page; JP Patent, XP–002114107.

Clausen, K., et al., "Studies on amino acids and peptides. II. Synthesis of protected endothiodipeptides," *J. Chem. Scr.,* 1982, 20(1–2), 14–18, doc. No. 97:163474 (abstract only, 1 page).

Corey, E.J. et al., "A Synthetic Method for Formyl → Ethynyl Conversion (RCHO → RC≡CH or RC≡CR')," *Tetrahedron Lett.,* 1972, 36, 3769–3772.

Cornforth, J.W., "Oxazoles and Oxazolones," *Chem. Penicillin,* Princeton Book Review, 1949, pp. 688, 799, and 800.

Davies, S..G., et al., "Asymmetric synthesis of R–β–amino butanoic acid and S–β–tyrosine: homochiral lithium amide equivalents for Michael additions to α,β–unsaturated esters," *Tetra. Asymmetry,* 1991, 2(3), 183–186.

Erle, D.J., et al., "Expression and function of the MadCAM–1 receptor, integrin α4β7, on human leukocytes," *J. Immunol.,* 1994, 153, 517–528.

Ferguson, T.A. et al., "Two integrin–binding peptides abrogate T cell–mediated immune responses in vivo," *Proc. Natl. Acad. Sci. USA,* 1991, 88, 8072–8076.

Frank, R., et al., "Extremely mild reagent for Boc deprotection," *Chem. Commun. (Cambridge),* 1996, 22, 2509–2510, doc. No. 126:104395 (abstract only, 3 pages).

Fu, H. et al., "Preliminary study on synthesis and antitumor activity in vitro of derivatives of timonacic," *Chemicals Abstracts,* 1988, 108(17), Abstract No. 150358k, 1 page.

Giacomello, et al., "Synthesis of 2,6–naphthyridine," *Tetra. Letters,* 1965, 16, 1117–1121.

Hammes, H., et al., "Subcutaneous injection of a cyclic peptide antagonist of vitronectin receptor–type integrins inhibits retinal neovascularization," *Nature Medicine,* 1996, 2, 529–533.

Harris, R.L.N. et al., *Aust. J. Chem.,* "Potential wool growth inhibitors. 2(1H)–Pyridone analogs of mimosine," 1977, 30(3), 649–655.

Hartke, K. et al., "Dithio and thiono esters. Part 61. Synthesis of α–amino dithioesters and endothiodipeptides,", *J. Prakt. Chem.,* 1996, 338(3), 251–256.

Hodivala–Dilke, K.M., "β3–integrin–deficient mice are a model for glanzmann thrombasthenia showing placental defects and reduced survival," *J. Clin. Invest.,* 1999, 103(2), 229–238.

Holzmann, B., et al., "Peyer's patch–specific lymphocyte homing receptors consist of a VLA–4–like α chain associated with either of two integrin β chains, one of which is novel," *EMBO J.,* 1989, 8(6), 1735–1741.

Humphries, M.J. et al., "Mechanisms of VCAM–1 and fibronectin binding to integrin $\alpha_4\beta_1$: implications for integrin function and rational drug design," *Ciba Foundation Symposium,* 1995, 189, 177–194.

Issekutz, T.B., "Inhibition of Lymphocyte Endothelial Adhesion and In Vivo Lymphocyte Migration to Cutaneous Inflammation by TA–3, a New Monoclonal Antibody to Rat LFA–1," *J. Immunol.,* 1992, 149(10), 3394–3402.

Jaynes, B.H. et al., "Synthesis and In Vivo Antibacterial Activity of Hygromycin a Analogs Modified at the $C_4'$ Aryl Position," *Bioorg. Med. Chem. Letts.,* 1993, 3(8), 1531–1536.

Jepson, J.B. et al., "Reactions of α–Thioacylamino–acids. Their conversion into Thiazolones and Derivatives Thereof," *J. Chem. Soc.,* 1955, 1791–1797.

Kalvin, D.M., et al., Synthesis of (4R)–D,L–[4–$^2$H]– and (4S)–D,L–[4–$^2$H] homoserine lactones, *J. Org. Chem.,* 1985, 50, 2259–2263.

Keenan, R.M. et al., "Discovery of Potent Nonpeptide Vitronectin Receptor (avβ$_3$) Antagonists," *J. Med. Chem.,* 1997, 40(15), 2289–2292.

Kobayashi, A., et al., "Syntheses of 2–dialkylamino–4, 4–disubstituted 5 (4H)–thiazolones," *J. Yakugaku Zasshi,* 1970, 90(11), 1377–1380, doc. No. 74:31713 (abstract only, 3 pages).

Koenig, H.B., et al., ".beta.–Lactam antibiotics," *Ger. Offen.,* 41 pages, doc. No. 83:97276 (abstract only, 5 pages); German patent.

Koivunen, E., et al., "Selection of peptides binding to the $\alpha_5\beta_1$ integrin from phage display library," *J. Biological Chemistry,* 1993, 268(27), 20205–20210.

Lei, H. et al., "Efficient Synthesis of a Phosphinate Bis–Amino Acid and Its Use in the Construction of Amphiphilic Peptides," *J. Org. Chem.,* 1994, 59, 4206–4210.

Li, Z. et al., "Effect of an anti–Mo1 MAb on ozone–induced airway inflammation and airway hyperresponsiveness in dogs," *Am. J. Physiol.,* 1992, 263(6 Pt 1), L723–726.

Lobb, R.R., et al., "Small molecule antagonists of alpha4 integrins: novel drugs for asthma," *Exp. Opin. Invest. Drugs,* 1999, XP000885957, 8(7), 935–945.

Marlin, S.D. et al., "LFA–1 Immunodeficiency Disease," *J. Exp. Med.,* 1986, 164, 855–867.

Masahiko, N., Japanese Patent No. 57–080370 published May 19, 1982, "Alpha–Methylcinnamic Acid Derivative, its Preparation and Antilipemic Agent Containing The Same," *Patent Abstracts of Japan,* 1982, 1 page.

Masuda, T., *Jpn. Kodai Tokkyo Koho,* 22 pages, doc. No. 115:280022 (abstract only, 1 page); JP patent.

McDowell, R.S. et al., "From Peptide to Non–Peptide. 2. The de Novo Design of Potent, Non–Peptidal Inhibitors of Platelet Aggregation Based on a Benzodiazepinedione Scaffold," *J. Am. Chem. Soc.,* 1994, 116, 5077–5083.

Miller, W.H. et al., "Structure–Activity Relationships in 3–Oxo–1,4–Benzodiazepine–2–Acetic Acid GPIIb/IIIa Antagonists. The 2–Benzazepine Series," *Bioorg. Med. Chem. Lett.,* 1996, 6(21), 2481–2486.

Mitjans, F., et al., "An anti–αv–integrin antibody that blocks integrin function inhibits the development of a human melanoma in nude mice," *J. Cell Science,* 1995, 108, 2825–2838.

Molina, P., et al., "Iminophosphorane–mediated annelation of a pyridine ring into a preformed pyridine one: synthesis of naphthyridine, pyrido [1,2–c] pyrimidine and pyrido [1,2–c] quinazoline derivatives," *Tetrahedron,* 1992, 48(22), 4601–4616.

Nagasawa, H.T. et al., "β–Substituted Cysteines as Sequestering Agents for Ethanol–Derived Acetaldehyde in Vivo," *J. Med. Chem.,* 1987, 30, 1373–1378.

Newham, P., et al., "Integrin adhesion receptors: structure, function and implications for biomedicine," *Nolecular Medicine Today,* 1996, 304–313.

Noike, Y., "Synthesis of Quinolizine Derivatives. VI. Synthesis of 3–Aminoquinolizines. (1). Synthesis of dl–3–Amino–, dl–3–epi–Amino–, and dl–3–epi–Dimethylaminoquinolizidines," *Yakugaku Zasshi,* 1959, 79(12), 1514–1518 (English summary included).

Numata, A., et al., "General synthetic method for naphthyridines and their N–oxides containing isoquinolinic nitrogen," *Synthesis,* 1999, 2, 306–311.

Ohki, S. et al., "Synthesis of quinolizine derivatives. V. Studies on Diastereoisomer of Ethyl 3–Quinolizidinecarboxylate," *Chem. Pharm. Bull.,* 1959, 7(6), 708–712.

Osborne, L., "Leukocyte Adhesion to Endothelium in Inflammation," *Cell,* 1990, 62, 3–6.

Osborn, L. et al., "Direct Expression Cloning of Vascular Cell Adhesion Molecule 1, a Cytokine–Induced Endothelial Protein that Binds to Lymphocytes," *Cell,* 1989, 59, 1203–1211.

Podolsky, D.K. et al., "Attenuation of Colitis in the Cotton–top Tamarin by Anti–α4 integrin Monoclonal Antibody," *J. Clin. Invest.,* 1993, 92, 372–380.

Pfeifer, T., et al., "Specific fragmentation of thioxo peptides facilitates the assignment of the thioxylated amino acid," *J. Mass Spectrom,* 1997, 32(10), 1064–1071, doc. No. 127:331738 (abstract only 2 pages).

Sakamoto, T., et al., "Condensed heteroaromatic ring systems. III. synthesis of naphthyridine derivatives by cyclization of ethynylpyridinecarboxamides," *Chem. Pharm. Bull.* 1985, 33(2), 626–633.

Samanen, J., et al., "Vascular indications for integrin alpha V antagonists," *Current Pharm. Design.,* 1997, 3, 545–584.

Šavrda, J., "CIS–TRANS isomerism of N–ACYL derivatives proline and its analogues, linear peptides with CIS peptide bonds," *Proc. 14$^{th}$ European Peptide Symposium,* Loffet, A. (ed.), 1976, 653–656.

Sawa, N., et al., "Preparation of 4(5)–thiocarbamoylimidazole compounds," *Jpn. Kokai Tokkyo Koho,* 33 pages, doc. No. 115:183296 (abstract only, 2 pages); JP patent.

Schultz, Von O.–E. et al., "Analogs of nuceic acid bases as antimetabolites," *Arzneimittel Forschung. Drug Res.,* 1967, 17(8), 1060–1064 (English summary included).

Schutkowski, M., et al., "Inhibition of peptidyl–prolyl cis/trans isomerase activity by substrate analog structures: thioxo tetrapeptide–4–nitroanilides," *Biochemistry,* 1995, 34(40), 13016–13026.

Schroff, H.N., et al., "Small peptide inhibitors of $α_4β_7$ mediated MadCAM–1 adhesion to lymphocytes," *Bioorg. Med. Chem. Letts.,* 1996, 6(21), 2495–2500.

Singh, G., et al., "Prodrug approach in new drug design and development," *J. Sci. Ind. Res.,* 1996, 55, 497–510.

Sonnenberg, A., "Integrins and their ligands," *Curr. Topics Microbiol. Immunol.,* 1993, 184, 7–35.

Springer, T.A., "Adhesion receptors of the immune system," *Nature,* 1990, 346, 425–434.

Springer, T.A., "Traffic Signals for Lymphocyte Recirculation and Leukocyte Emigration: The Multistep Paradigm," *Cell,* 1994, 76, 301–314.

Srivatsa, S.S., et al., "Selective αvβ3 integrin blockade potently limits neointimal hyperplasia and lumen stenosis following deep coronary arterial stent injury: evidence for the functional importance of integrin αvβ3 and osteopontin expression during neointima formation," *Cariovascular Research,* 1997, 36, 408–428.

Stupack, D.G., et al., "induction of $α_vβ_3$ integrin–mediated attachment to extracellular matrix in $β_1$ integrin (CD29)–negative B cell lines," *Experi. Cell Research,* 1992, 203, 443–448.

Tan R., et al., "Synthesis of 2, 6–naphthyridine and some of its derivatives," *Tetrahedron Letters,* 1965, 31, 2737–2744.

Tous, G., et al., "O'–(Epoxyalkyl) tyrosines and (Epoxyalkyl) phenylalanine as irreversible inactivators of serine proteases: synthesis and inhibition mechanism," *J. of Medicinal Chemistry,* 1990, 33(6), 1620–1634.

Tsunematsu, H. et al., "Hydrolysis of phenylthiazolones of p–guanidinophenylalanine and arginine by trypsin and related enzymes," *J. Biochem.,* 1983, 94(4), 1119–1125.

Ukai, Y. et al., "A novel synthetic inhibitor of endopeptidase–24.15," *Chemical Abstracts,* 1997, 127(2), 1 page; J. Enzym Inhib., 1996, 11(1), 39–49, reported in CAS.

Vanderslice, P. et al., "A Cyclic Hexapeptide is a Potent Antagonist of α4 Integrins," *J. Immunol.,* 1997, 158, 1710–1718.

Venturella, V.S. et al., "Substituted 1,3–Dihydro–4H–furo [3,4–d]–1,3–benzodiazepin–3–ones: Synthesis and Scope of the Method," *J. Heterocyclic Chem.,* 1969, 6(5), 671–679.

Yanagisawa, H. et al., WO 97/37970, "Preparation of phenylalkylcarboxylic acid derivatives lowering blood sugar level," *Chemical Abstracts,* 1997, Abstract 127:307307, 4 pages.

Yang, X., "A predominant role of integrin α4 in the spontaneous development of autoimmune diabetes in nonobese diabetic mice," *Proc. Natl. Acad. Sci. USA,* 1994, 91, 12604–12608.

Yednock, T.A., "Prevention of experimental autoimmune encephalomyelitis by antibodies against α4β1 integrin," *Nature,* 1992, 356, 63–66.

Whitlock, B.J. et al., "Structure and synthesis of lathyrine," *J. Org. Chem.,* 1965, 30, 115–118.

Wojciechowska, H. et al., "Preparation of 2,4-dinitrophenyl derivatives of tyrosine," *Chemical Abstracts,* 1968, 68(25), Abstract No. 114926r, 1 page, *Roc. Chem.,* 1967, 41(9), 1621–1623; reported in CAS.

WPI / Derwent No. XP-002076854, Japanese Patent No. JP 04 193 895 A (Ajinomoto, K.K.), Jul. 13, 1992, DW9234, 1 Page, Abstract Only.

WPI/Derwent No. XP-002076855, Japanese Patent No. JP 56 049 373 A (Dainippon Pharm Co. Ltd.), May 2, 1981, DW8125, 1 page, Abstract only.

Hammadi, A., et al., "Diastereoselective hydrogenation of monodehydro enkephalins controlled by chiral rhodium catalysts," *Tetrahedron: Asymmetry,* 1992, 3(10), XP002106601, 1247–1262.

Nunami, K., et al., "A novel synthesis of methyl 1,5-disubstituted imidazole-4-carboxylates using 3-bromo-2-isocyanoacrylates," *J. Org. Chem.,* 1994, 59, XP002106602, 7635–7642.

Shimohigashi, Y., et al., "Dehydro-enkephalins," *Int. J. Peptide Protein Res.,* 1983, 21, XP002106600, 202–208.

Strange, P.G., et al., "Studies of enzyme-mediated reactions. Part II. Stereochemistry of the elimination of ammonia form L-tyrosine catalysed by the enzyme from maize," *J. Chem. Soc., Perkin I,* 1972, 18, XP002106603, 2364–2372.

WPI/Derwent No. XP002106604, Japanese Patent No. JP 60 190749 (Mitsui Toatsu Chem. Inc.), Sep. 28, 1985, 1 page, Abstract only.

Rico, J.G., et al., "A highly steroselective michael addition to an αβ-unsaturated ester as the crucial step in the synthesis of a novel β-amino acid-containing fibrinogen receptor antagonist," *J. Org. Chem.,* 1993, 58, 7948–7951.

Zablocki, J.A., "Potent in vitro and in vivo inhibitors of platelet aggregation based upon the arg-gly-asp sequence of fibrinogen. (Aminobenzamidino)succinyl (ABAS) series of orally active fibrinogen receptor antagonists," *J. Med. Chem.,* 1995, 38, 2378–2394.

\* cited by examiner

SQUARIC ACID DERIVATIVES

This invention relates to a series of bicyclic heteroaromatic derivatives, to compositions containing them, to processes for their preparation, and to their use in medicine.

Over the last few years it has become increasingly clear that the physical interaction of inflammatory leukocytes with each other and other cells of the body plays an important role in regulating immune and inflammatory responses [Springer, T. A., Nature, 346, 425, (1990); Springer, T. A., Cell, 76, 301, (1994)]. Specific cell surface molecules collectively referred to as cell adhesion molecules mediate many of these interactions.

The adhesion molecules have been sub-divided into different groups on the basis of their structure. One family of adhesion molecules which is believed to play a particularly important role in regulating immune and inflammatory responses is the integrin family. This family of cell surface glycoproteins has a typical non-covalently linked heterodimer structure. At least 16 different integrin alpha chains and 8 different integrin beta chains have been identified [Newman, P. et al, Molecular Medicine Today, 304, (1996)]. The members of the family are typically named according to their heterodimer composition although trivial nomenclature is widespread in the field. Thus the integrin $\alpha 4\beta 1$ consists of the integrin alpha 4 chain associated with the integrin beta 1 chain, but is also widely referred to as Very Late Antigen 4 or VLA-4. Not all of the potential pairings of integrin alpha and beta chains have yet been observed in nature and the integrin family has been subdivided into a number of subgroups based on the pairings that have been recognised to date [Sonnenberg, A., Current Topics in Microbiology and Immunology, 184, 7, (1993)].

The importance of integrin function in normal physiological responses is highlighted by two human deficiency diseases in which integrin function is defective. Thus in the disease termed Leukocyte Adhesion Deficiency (LAD) there is a defect in one of the families of integrins expressed on leukocytes [Marlin, S. D. et al, J. Exp. Med. 164, 855, (1986)]. Patients suffering from this disease have a reduced ability to recruit leukocytes to inflammatory sites and suffer recurrent infections, which in extreme cases may be fatal. In the case of patients suffering from the disease termed Glanzman's thrombasthenia (a defect in a member of the beta 3 integrin family) there is a defect in blood clotting (Hodivala-Dilke, K. M., J. Clin. Invest. 103, 229, (1999)].

The potential to modify integrin function in such a way as to beneficially modulate cell adhesion has been extensively investigated in animal models using specific antibodies and peptides that block various functions of these molecules [e.g. Issekutz, T. B., J. Immunol. 149, 3394, (1992); Li, Z. et al, Am. J. Physiol. 263, L723, (1992); Mitjans, F. et al, J. Cell Sci. 108, 2825, (1995); Brooks, P. C. et al, J. Clin. Invest. 96, 1815, (1995); Binns, R. M. etal, J. Immunol. 157, 4094, (1996); Hammes, H. -P. et al, Nature Medicine 2, 529, (1996); Srivata, S. et al, Cardiovascular Res. 36, 408 (1997)]. A number of monoclonal antibodies which block integrin function are currently being investigated for their therapeutic potential in human disease, and one, ReoPro, a chimeric antibody against the platelet integrin $\alpha IIb\beta 3$ is in use as a potent anti-thrombotic agent for use in patients with cardiovascular complications following coronary angioplasty. Integrins recognize both cell surface and extracellular matrix ligands, and ligand specificity is determined by the particular alpha-beta subunit combination of the molecule [Newman, P., ibid]. One particular integrin subgroup of interest involves the $\alpha 4$ chain which can pair with two different beta chains $\beta 1$ and $\beta 7$ [Sonnenberg, A., ibid]. The $\alpha 4\beta 1$ pairing occurs on many circulating leukocytes (for example lymphocytes, monocytes, eosinophils and basophils) although it is absent or only present at low levels on circulating neutrophils. $\alpha 4\beta 1$ binds to an adhesion molecule (Vascular Cell Adhesion Molecule-1 also known as VCAM-1) frequently up-regulated on endothelial cells at sites of inflammation [Osborne, L., Cell, 62, 3, (1990)]. The molecule has also been shown to bind to at least three sites in the matrix molecule fibronectin [Humphries, M. J. et al, Ciba Foundation Symposium, 189, 177, (1995)]. Based on data obtained with monoclonal antibodies in animal models it is believed that the interaction between $\alpha 4\beta 1$ and ligands on other cells and the extracellular matrix plays an important role in leukocyte migration and activation [Yednock, T. A. et al, Nature, 356, 63, (1992); Podolsky, D. K. et al, J. Clin. Invest. 92, 372, (1993); Abraham, W. M. et al, J. Clin. Invest. 93, 776, (1994)].

The integrin generated by the pairing of $\alpha 4$ and $\beta 7$ has been termed LPAM-1 [Holzmann, B. and Weissman, I. L., EMBO J. 8, 1735, (1989)]. The $\alpha 4\beta 7$ pairing is expressed on certain sub-populations of T and B lymphocytes and on eosinophils [Erie, D. J. et al, J. Immunol. 153, 517 (1994)]. Like $\alpha 4\beta 1$, $\alpha 4\beta 7$ binds to VCAM-1 and fibronectin. In addition, $\alpha 4\beta 7$ binds to an adhesion molecule believed to be involved in the homing of leukocytes to mucosal tissue termed MAdCAM-1 [Berlin, C. et al, Cell, 74, 185, (1993)]. The interaction between $\alpha 4\beta 7$ and MAdCAM-1 may also be important sites of inflammation outside of mucosal tissue [Yang, X. -D. et al, PNAS, 91,12604, (1994)].

Regions of the peptide sequence recognizeded by $\alpha 4\beta 1$ and $\alpha 4\beta 7$ when they bind to their ligands have been identified. $\alpha 4\beta 1$ seems to recognise LDV, IDA or REDV peptide sequences in fibronectin and a QIDSP sequence in VCAM-1 [Humphries, M. J. et al, ibid] whilst $\alpha 4\beta 7$ recognises a LDT sequence in MAdCAM-1 [Birskin, M. J. et al, J. Immunol. 156, 719, (1996)]. There have been several reports of inhibitors of these interactions being designed from modifications of these short peptide sequences [Cardarelli, P. M. et al, J. Biol. Chem., 269, 18668, (1994); Shorff, H. N. et al, Biorganic Med. Chem. Lett., 6, 2495, (1996); Vanderslice, P. et al, J. Immunol., 158, 1710, (1997)]. It has also been reported that a short peptide sequence derived from the $\alpha 4\beta 1$ binding site in fibronectin can inhibit a contact hypersensitivity reaction in a trinitrochlorobenzene sensitised mouse [Ferguson, T. A., et al, PNAS, 88, 8072, (1991)].

Since the alpha 4 subgroup of integrins are predominantly expressed on leukocytes their inhibition can be expected to be beneficial in a number of immune or inflammatory disease states. However, because of the ubiquitous distribution and wide range of functions performed by other members of the integrin family it is important to be able to identify selective inhibitors of the alpha 4 subgroup.

We have now found a group of bicyclicheteroaromatic compounds which are potent and selective inhibitors of $\alpha 4$-integrins. Members of the group are able to inhibit $\alpha 4$ integrins such as $\alpha 4\beta 1$ and $\alpha 4\beta 7$ at concentrations at which they generally have no or minimal inhibitory action on $\alpha$ integrins of other subgroups. These compounds also possess good pharmacokinetic properties, especially low plasma clearance. The compounds are thus of use in medicine, for example in the prophylaxis and treatment of immune or inflammatory disorders as described hereinafter.

Thus according to one aspect of the invention we provide a compound of formula (1):

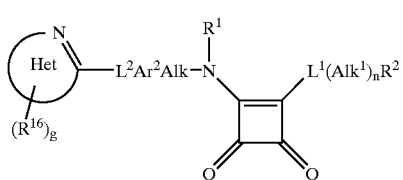

wherein
Het is a bicyclic fused ring heteroaromatic group;
g is zero or the integer 1, 2, 3 or 4;
Each $R^{16}$, which may be the same or different is an atom or group —$L^3(Alk^2)_tL^4(R^4)_u$ in which $L^3$ and $L^4$, which may be the same or different, is each a covalent bond or a linker atom or group, t is zero or the integer 1, u is an integer 1, 2 or 3, $Alk^2$ is an aliphatic or heteroaliphatic chain and $R^4$ is a hydrogen or halogen atom or a group selected from optionally substituted $C_{1-6}$alkyl or $C_{3-8}$ cycloalkyl, —$OR^5$ [where $R^5$ is a hydrogen atom, an optionally substituted $C_{1-6}$alkyl or $C_{3-8}$ cycloalkyl group], —$SR^5$, —$NR^5R^6$ [where $R^6$ is as just defined for $R^5$ and may be the same or different], —$NO_2$, —$CN$, —$CO_2R^5$, —$SO_3H$, —$SOR^5$, —$SO_2R^5$, —$SO_3R^5$, —$OCO_2R^5$, —$CONR^5R^6$, —$OCONR^5R^6$, —$CSNR^5R^6$, —$COR^5$, —$N(R^5)COR^6$, —$N(R^5)CSR^6$, —$SO_2N(R^5)(R^6)$, —$N(R^5)SO_2R^6$ $^{N(R5)}CON(R^6)(R^7)$ [where $R^7$ is a hydrogen atom, an optionally substituted $C_{1-6}$alkyl or $C_{3-8}$cycloalkyl group], —$N(R^5)CSN(R^6)(R^7)$ or —$N(R^5)SO_2N(R^6)(R^7)$, provided that when t is zero and each of $L^3$ and $L^4$ is a covalent bond then u is the integer 1 and $R^4$ is other than a hydrogen atom;
$L^2$ is a covalent bond or an atom or group —O—, —S—, —C(O)—, —C(S)—, —S(O)—, —S(O)$_2$, —N($R^8$)— [where $R^8$ is a hydrogen atom or an optionally substituted $C_{1-6}$alkyl group] or —C($R^8$)($R^{8a}$)— [where $R^{8a}$ is an atom or group as defined for $R^8$ and may be the same or different];
$Ar^2$ is an optionally substituted aromatic or heteroaromatic group;
Alk is a chain

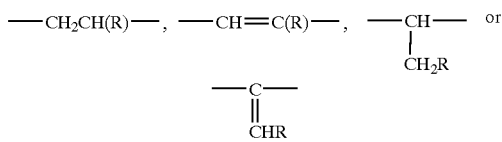

in which R is a carboxylic acid (—$CO_2H$) or a derivative or biostere thereof;
$R^1$ is a hydrogen atom or a $C_{1-6}$alkyl group;
$L^1$ is a covalent bond or a linker atom or group;
$Alk^1$ is an optionally substituted aliphatic chain;
n is zero or the integer 1;
$R^2$ is a hydrogen atom or an optionally substituted heteroaliphatic, cycloaliphatic, heterocycloaliphatic, polycycloalphatic, heteropolycycloaliphatic, aromatic or heteroaromatic group;
provided that Het is not a 2,6-naphthyridin-1-yl, isoquinolin-1-yl, 2,7-naphthyridin-1-yl or quinazolin-4-yl group;

and the salts, solvates, hydrates and N-oxides thereof.

It will be appreciated that compounds of formula (1) may have one or more chiral centres, and exist as enantiomers or diastereomers. The invention is to be understood to extend to all such enantiomers, diastereomers and mixtures thereof, including racemates. Formula (1) and the formulae hereinafter are intended to represent all individual isomers and mixtures thereof, unless stated or shown otherwise. In addition, compounds of formula (1) may exist as tautomers, for example keto(—$CH_2C$=O)-enol-(CHCHOH) tautomers. Formula (1) and the formulae hereinafter are intended to represent all individual tautomers and mixtures thereof, unless stated otherwise.

Bicyclic fused ring heteroaromatic groups represented by Het in the compounds of formula (1) include those bicyclic fused ring heteroaromatic groups containing a N heteroatom adjacent to the carbon atom that joins the Het group to the remainder of the compound of formula (1). Bicyclic heteroaromatic groups of this type include for example eight- to thirteen-membered fused-ring heteroaromatic groups containing one, two, three or more further heteroatoms selected from oxygen, sulphur or nitrogen atoms. Particular examples of heteroaromatic groups of this type include indol-2-yl, indazol-3-yl, benzoimidazol-2-yl, benzoxazol-2-yl, benzisoxazol-3-yl, benzthiazol-2-yl, purin-8-yl, purin-6-yl, purin-2-yl, quinolin-2-yl, cinnolin-3-yl, phthalazin-1-yl, quinoxalin-2-yl, pyrano[3,4-b]pyrrol-2-yl, pyrido[3,4-b]pyridin-2-yl, pyrido[3,4-b]pyridin-8-yl, pyrido[3,2-b]pyridin-2-yl, pyrido[4,3-b]pyridin-2-yl, pyrido[4,3-b]pyridin-5-yl, 1H-imidazo[4,5-b]pyrazin-2-yl, imidazo[1,5-a]pyridin-3-yl, 1H-imidazo[4,5-b]pyridin-2-yl, 1H-imidazo[4,5-c]pyridin-2-yl and pteridin-4-yl groups.

Further bicyclic fused ring heteroaromatic groups represented by Het in the compounds of formula (1) include groups of formula:

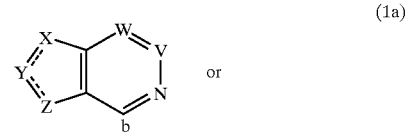

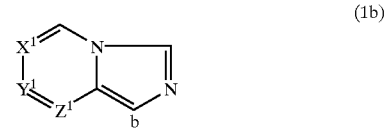

in which V and W is each independently selected from a nitrogen atom or a CH group, provided that both V and W are not nitrogen atoms, X, Y and Z is each independently selected from a nitrogen, oxygen or sulphur atom or CH group, $X^1$, $Y^1$ and $Z^1$ is each independently selected from a nitrogen atom or a CH group provided that when two of $X^1$, $Y^1$ and $Z^1$ are nitrogen atoms the other is a CH group, the broken line ( - - - ) represents saturation or unsaturation and the carbon atom identified by the letter b represents the point of attachment to the group $L^2Ar^2$ in compounds of formula (1).

In bicyclic fused ring heteroaromatic groups represented by formula (1a) the partial ring structure:

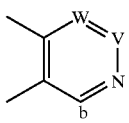

includes for example optionally substituted rings selected from

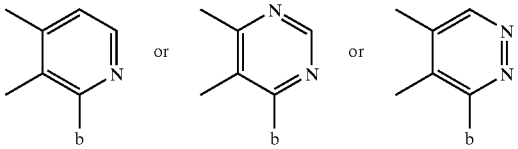

In fused ring bicyclic heteroaromatic groups represented by formula (1a) the partial ring structure:

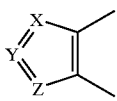

includes for example optionally substituted rings selected from:

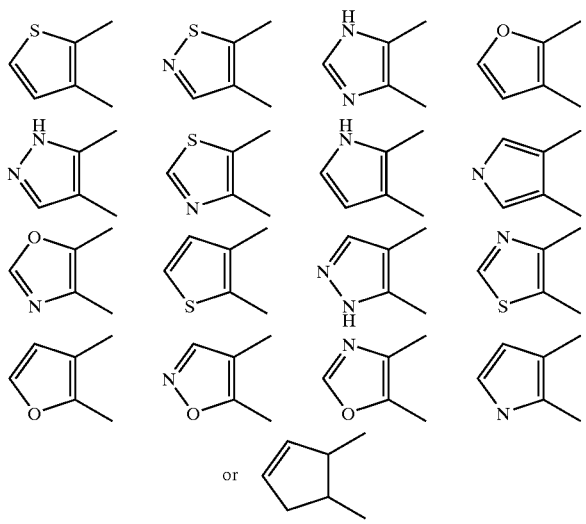

In fused ring bicyclic heteroaromatic groups represented by formula (1b) the partial ring structure:

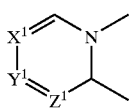

includes for example optionally substituted rings selected from:

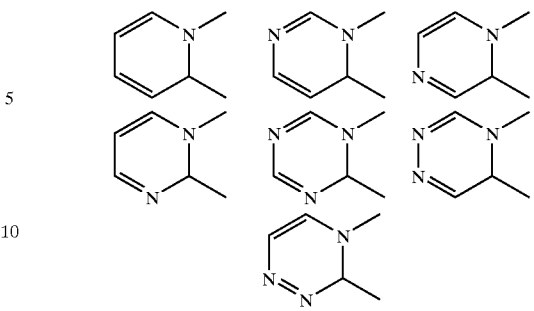

Optional substituents which may be present on any available carbon atom of the bicyclic fused ring heteroaromatic groups represented by Het include those $R^{16}$ atoms and groups as previously defined and as described hereinafter.

When $L^3$ and/or $L^4$ is present in the optional $R^{16}$ substituents in compounds of formula (1) as a linker atom or group it may be any divalent linking atom or group. Particular examples include —O— or —S— atoms or —C(O)—, —C(O)O—, —OC(O)—, —C(S)—, —S(O)—, —S(O)$_2$—, —N($R^8$)— [where $R^8$ is as previously defined], —N($R^8$)O—, —N($R^8$)N—, —CON($R^8$)—, —OC(O)N ($R^8$)—, —CSN($R^8$)—, —N($R^8$)CO—, —N($R^8$)C(O)O—, —N($R^8$)CS—, —S(O)$_2$N($R^8$)—, —N($R^8$)S(O)$_2$—, —N($R^8$)CON($R^8$)—, —N($R^8$)CSN($R^8$)—, or —N($R^8$)SO$_2$N($R^8$)— groups. Where the linker group contains two $R^8$ substituents, these may be the same or different.

When $R^4$, $R^5$, $R^6$, $R^7$ and/or $R^8$ is present as a $C_{1-6}$alkyl group it may be a straight or branched $C_{1-6}$alkyl group, e.g. a $C_{1-3}$alkyl group such as a methyl, ethyl, propyl or 1-propyl group. $C_{3-8}$cycloalkyl groups represented by $R^4$, $R^5$, $R^6$, $R^7$ and/or $R^8$ include $C_{3-6}$cycloalkyl groups e.g. cyclopropyl, cyclobutyl, cyclopentyl and cyclohexyl groups. Optional substituents which may be present on such groups include for example one, two or three substituents which may be the same or different selected from halogen atoms, for example fluorine, chlorine, bromine or iodine atoms, or hydroxy or $C_{1-6}$alkoxy e.g. methoxy or ethoxy groups.

When the groups $R^5$ and $R^6$ or $R^6$ and $R^7$ are both $C_{1-6}$alkyl groups these groups may be joined, together with the N atom to which they are attached, to form a heterocyclic ring. Such heterocyclic rings may be optionally interrupted by a further heteroatom selected from —O—, —S— or —N($R^5$)—. Particular examples of such heterocyclic rings include piperidinyl, morpholinyl, thiomorpholinyl, pyrrolidinyl, imidazolidinyl and piperazinyl rings.

When $Alk^2$ is present as an aliphatic or heteroaliphatic chain in the optional $R^{16}$ substituents represented by —$L^3$ $(Alk^2)_t L^4(R^4)_u$ it may be for example any divalent chain corresponding to the below-mentioned aliphatic chains described for $Alk^1$ or heteroaliphatic groups described for $R^2$ in which one of the terminal hydrogen atoms is replaced by a bond.

Halogen atoms represented by $R^4$ in the optional $R^{16}$ substituents include fluorine, chlorine, bromine, or iodine atoms.

Examples of the substituents represented by —$L^3(Alk^2)_t L^4(R^4)_u$ when present as $R^{16}$ atoms or groups in compounds of the invention include atoms or groups —$L^3Alk^2L^4R^4$, —$L^3Alk^2R^4$, —$L^3R^4$, —$R^4$ and —$Alk^2R^4$ wherein $L^3$, $Alk^2$, $L^4$ and $R^4$ are as defined above. Particular examples of such substituents include —$L^3CH_2L^4R^4$, —$L^3CH(CH_3)L^4R^4$, —$L^3CH(CH_2)_2L^4R^4$, —$L^3CH_2R^4$, —$L^3CH(CH_3)R^4$, —$L^3(CH_2)_2R^4$, —$CH_2R^4$, —$CH(CH_3R^4$, —$(CH_2)_2R^4$, and —$R^4$ groups.

Thus the Het group in compounds of the invention may be optionally substituted for example by one, two, three or four $R^{16}$ atoms or groups whee $R^{16}$ may be a halogen atom, e.g. fluorine, chlorine, bromine or iodine atom, and/or $C_{1-6}$alkyl, e.g. methyl, ethyl, n-propyl, 1-propyl, n-butyl or t-butyl, $C_{3-8}$cycloalkyl, e.g. cyclopropyl, cyclobutyl, cyclopentyl or cyclohexyl, $C_{1-6}$hydroxyalkyl, e.g. hydroxymethyl, hydroxyethyl or —C(OH)(CF$_3$)$_2$, carboxy$C_{1-6}$alkyl, e.g. carboxyethyl, $C_{1-6}$alkylthio e.g. methylthio or ethylthio, carboxy$C_{1-6}$alkylthio, e.g. carboxymethylthio, 2-carboxyethylthio or 3-carboxypropylthio, $C_{1-6}$alkoxy, e.g. methoxy or ethoxy, hydroxy$C_{1-6}$alkoxy, e.g. 2-hydroxyethoxy, halo$C_{1-6}$alkyl, e.g. —CF$_3$ or —CHF$_2$, or —CH$_2$F, halo$C_{1-6}$alkoxy, e.g. —OCF$_3$, —OCHF$_2$ or —OCH$_2$F, $C0_{1-6}$alkylamino, e.g. methylamino or ethylamino, amino (—NH$_2$), amino$C_{1-6}$alkyl, e.g. aminomethyl or aminoethyl, $C_{1-6}$dialkylamino, e.g. dimethylamino or diethylamino, $C_{1-6}$alkylamino$C_{1-6}$alkyl, e.g. ethylaminoethyl, $C_{1-6}$ dialkylamino$C_{1-6}$alkyl, e.g. diethylaminoethyl, amino$C_{1-6}$alkoxy, e.g. aminoethoxy, $C_{1-6}$alkylamino$C_{1-6}$alkoxy, e.g. methylaminoethoxy, $C_{1-6}$dialkylamino$C_{1-6}$alkoxy, e.g. dimethylaminoethoxy, diethylaminoethoxy, diisopropylaminoethoxy, or dimethylaminopropoxy, nitro, cyano, amidino, hydroxyl (—OH), formyl [HC(O)—], carboxyl (—CO$_2$H), —CO$_2$Alk$^3$ [where Alk$^3$ is as defined below for Alk$^7$], $C_{1-6}$ alkanoyl e.g. acetyl, thiol (—SH), thio$C_{1-6}$alkyl, e.g. thiomethyl or thioethyl, sulphonyl (—SO$_3$H), —SO$_3$Alk$^3$, $C_{1-6}$alkylsulphinyl, e.g. methylsulphinyl, $C_{1-6}$alkylsulphonyl, e.g. methylsulphonyl, aminosulphonyl (—SO$_2$NH$_2$), $C_{1-6}$ alkylaminosulphonyl, e.g. methylaminosulphonyl or ethylaminosulphonyl, $C_{1-6}$dialkylaminosulphonyl, e.g. dimethylaminosulphonyl or diethylaminosulphonyl, carboxamido (—CONH$_2$), $C_{1-6}$alkylaminocarbonyl, e.g. methylaminocarbonyl or ethylaminocarbonyl, $C_{1-6}$dialkylaminocarbonyl, e.g. dimethylaminocarbonyl or diethylaminocarbonyl, amino$C_{1-6}$alkylaminocarbonyl, e.g. aminoethylaminocarbonyl, $C_{1-6}$dialkylamino$C_{1-6}$alkylaminocarbonyl, e.g. diethylaminoethylaminocarbonyl, aminocarbonylamino, $C_{1-6}$alkylaminocarbonylamino, e.g. methylaminocarbonylamino or ethylaminocarbonylamino, $C_{1-6}$dialkylaminocarbonylamino, e.g. dimethylaminocarbonylamino or diethylaminocarbonylamino, $C_{1-6}$alkylaminocabonyl, $C_{1-6}$alkylamino, e.g. methylaminocarbonylmethylamino, aminothiocarbonylamino, $C_{1-6}$alkylaminothiocarbonylamino, e.g. methylaminothiocarbonylamino or ethylaminothiocarbonylamino, $C_{1-6}$dialkylaminothiocarbonylamino, e.g. dimethylaminothiocarbonylamino or diethylaminothiocarbonylamino, $C_{1-6}$alkylaminothiocarbonyl$C_{1-6}$alkylamino, e.g. ethylaminothiocarbonylmethylamino, $C_{1-6}$alkylsulphonylamino, e.g. methylsulphonylamino or ethylsulphonylamino, $C_{1-6}$dialkylsulphonylamino, e.g. dimethylsulphonylamino or diethyl-sulphonylamino, aminosulphonylamino (—NHSO$_2$NH$_2$), $C_{1-6}$alkylaminosulphonylamino, e.g. methylaminosulphonylamino or ethylaminosulphonylamino, $C_{1-6}$dialkylaminosulphonylamino, e.g. dimethylaminosulphonylamino or diethylaminosulphonylamino, $C_{1-6}$alkanoylamino, e.g. acetylamino, amino$C_{1-6}$alkanoylamino e.g. aminoacetylamino, $C_{1-6}$dialkylamino$C_{1-6}$alkanoylamino, e.g. dimethylaminoacetylamino, $C_{1-6}$alkanoylamino$C_{1-6}$alkyl, e.g. acetylaminomethyl, $C_{1-6}$alkanoylamino$C_{1-6}$alkylamino, e.g. acetamidoethylamino, $C_{1-6}$alkoxycarbonylamino, e.g. methoxycarbonylamino, ethoxycarbonylamino or t-butoxycarbonylamino group.

Optionally substituted aromatic or heteroaromatic groups represented by Ar$^2$ include those aromatic or heteroaromatic groups described hereinafter in relation to R$^2$ aromatic or heteroaromatic groups respectively. The optional substituents which may be present on these groups include those optional substituents described in relation to R$^2$ aromatic or heteroaromatic groups.

When the group R is present in compounds of the invention as a derivative of a carboxylic acid it may be for example a carboxylic acid ester or amide. Particular esters and amides include —CO$_2$Alk$^7$ and —CONR$^5$R$^6$ groups as defined herein. When R is a biostere of a carboxylic acid it may be for example a tetrazole or other acid such as phosphonic acid, phosphinic acid, sulphonic acid, sulphinic acid or boronic acid or an acylsulphonamide group.

Esters (—CO$_2$Alk$^7$) and amide (—CONR$^5$R$^6$) derivatives of the carboxylic acid group (—CO$_2$H) in compounds of formula (1) may advantageously be used as prodrugs of the active compound. Such prodrugs are compounds which undergo biotransformation to the corresponding carboxylic acid prior to exhibiting their pharmacological effects and the invention particularly extends to prodrugs of the acids of formula (1). Such prodrugs are well known in the art, see for example International Patent Application No. WO00123419, Bodor, N. (Alfred Benzon Symposium, 1982, 17, 156–177), Singh, G. et al (J. Sci. Ind. Res., 1996, 55, 497–510) and Bundgaard, H., (Design of Prodrugs, 1985, Elsevier, Amsterdam.

Esterified carboxyl groups represented by the group —CO$_2$Alk$^7$ include those wherein Alk$^7$ is a straight or branched optionally substituted $C_{1-8}$alkyl group such as a methyl, ethyl, n-propyl, 1-propyl, n-butyl, 1-butyl, s-butyl or t-butyl group; an optionally substituted $C_{2-8}$alkenyl group such as a propenyl e.g. 2-propenyl or butenyl e.g. 2-butenyl or 3-butenyl group, an optionally substituted $C_{2-8}$alkynyl group such as a ethynyl, propynyl e.g. 2-propynyl or butynyl e.g. 2-butynyl or 3-butynyl group, an optionally substituted $C_{3-8}$cycloalkyl group such as a cyclopropyl, cyclobutyl, cyclopentyl, cyclohexyl or cycloheptyl group; an optionally substituted $C_{3-8}$cycloalkyl$C_{1-8}$alkyl group such as a cyclopentylmethyl, cyclohexylmethyl or cyclohexylethyl group; an optionally substituted $C_{3-8}$heterocycloalkyl$C_{1-6}$alkyl group such as a morpholinyl-N-ethyl, thiomorpholinyl-N-methyl, pyrrolidinyl-N-ethyl, pyrrolidinyl-N-propyl, piperidinyl-N-ethyl, pyrazolidinyl-N-methyl or piperazinyl-N-ethyl group; an optionally substituted $C_{1-6}$alkyloxy$C_{1-6}$alkyl group such as a methyloxyethyl or propyloxyethyl group; an optionally substituted $C_{1-6}$alkylthio$C_{1-6}$alkyl group such as an ethylthioethyl group; an optionally substituted $C_{1-6}$alkylsulfinyl$C_{1-6}$alkyl group such as an methylsulfinylethyl group; an optionally substituted $C_{1-6}$alkylsulfonyl$C_{1-6}$alkyl group such as an methylsulfonylmethyl group; an optionally substituted $C_{3-8}$cycloalkyloxy$C_{1-6}$alkyl group such as a cyclohexyloxymethyl group; an optionally substituted $C_{3-8}$cycloalkylthio$C_{1-6}$alkyl group such as a cyclopentylthiomethyl group; an optionally substituted $C_{3-8}$cycloalkylsulfinyl$C_{1-6}$alkyl group such as a cyclopentylsulfinylmethyl group; an optionally substituted $C_{3-8}$cycloalkylsulfonyl$C_{1-6}$alkyl group such as a cyclopentylsulfonylmethyl group; an optionally substituted $C_{1-6}$alkyloxycarbonyl$C_{1-6}$alkyl group such as isobutoxycarbonylpropyl group; an optionally substituted $C_{1-6}$alkyloxycarbonyl$C_{1-6}$alkenyl group such as isobutoxycarbonylpentenyl group; an optionally substituted $C_{1-6}$alkyloxy-carbonyloxy$C_{1-6}$alkyl group such as an isopropoxycarbonyloxyethyl e.g a 1-(isopropoxycarbonyloxy)

ethyl, 2-(isopropoxycarbonyloxy)ethyl or ethyloxycarbonyloxymethyl group; an optionally substituted $C_{1-6}$alkyloxycarbonyloxy$C_{1-6}$alkenyl group such as a isopropoxycarbonyloxybutenyl group, an optionally substituted $C_{3-8}$cycloalkyloxycarbonyloxy$C_{1-6}$alkyl group such as a cyclohexyloxycarbonyloxyethyl, e.g. a 2-(cyclohexyloxycarbonyloxy)ethyl group, an optionally substituted N-di-$C_{1-8}$alkylamino$C_{1-8}$alkyl group such as a N-dimethylaminoethyl or N-diethylaminoethyl group; an optionally substituted N—$C_{6-12}$aryl-N—$C_{1-16}$alkylamino$C_{1-6}$alkyl group such as a N-phenyl-N-methylaminomethyl group; an optionally substituted N-di-$C_{1-8}$alkylcarbamoyl$C_{1-8}$alkyl group such as a N-diethylcarbamoylmethyl group; an optionally substituted $C_{6-10}$aryl$C_{1-6}$alkyl group such as an optionally substituted benzyl, phenylethyl, phenylpropyl, 1-naphthylmethyl or 2-naphthylmethyl group; a $C_{6-10}$aryl group such as an optionally substituted phenyl, 1-naphthyl or 2-naphthyl group; a $C_{6-10}$aryloxy$C_{1-8}$alkyl group such as an optionally substituted phenyloxymethyl, phenyloxyethyl, 1-naphthyloxymethyl, or 2-naphthyloxymethyl group; a $C_{6-12}$arylthio$C_{1-8}$alkyl group such as an optionally substituted phenylthioethyl group; a $C_{6-12}$arylsulfinyl$C_{1-8}$alkyl group such as an optionally substituted phenylsulfinylmethyl group; a $C_{6-12}$arylsulfonyl$C_{1-8}$alkyl group such as an optionally substituted phenylsulfonylmethyl group; an optionally substituted $C_{1-8}$alkanoyloxy$C_{1-8}$alkyl group, such as a acetoxymethyl, ethoxycarbonyloxyethyl, pivaloyloxymethyl, propionyloxyethyl or propionyloxypropyl group; an optionally substituted $C_{4-8}$imido$C_{1-8}$alkyl group such as a succinimidomethyl or phthalamidoethyl group; a $C_{6-12}$aroyloxy$C_{1-8}$alkyl group such as an optionally substituted benzoyloxyethyl or benzoyloxypropyl group or a triglyceride such as a 2-substituted triglyceride e.g. a 1,3-di-$C_{1-18}$alkylglycerol-2-yl group such as a 1,3-diheptylglycerol-2-yl group. Optional substituents present on the Alk$^7$ group include $R^{13a}$ substituents described above.

It will be appreciated that in the forgoing list of Alk$^7$ groups the point of attachment to the remainder of the compound of formula (1) is via the last described part of the Alk$^7$ group. Thus, for example a methoxyethyl group would be attached by the ethyl group, whilst a morpholinyl-N-ethyl group would be attached via the N-ethyl group.

It will be further appreciated that in the forgoing list of Alk$^7$ groups, where not specifically mentioned, alkyl groups may be replaced by alkenyl or alkynyl groups where such groups are as previously defined for the group Alk$^1$. Additionally these alkyl, alkenyl or alkynyl groups may optionally be interrupted by one, two or three linker atoms or groups where such linker atoms and groups are as previously defined for $L^3$.

When the group $R^1$ is present in compounds of the invention as a $C_{1-6}$alkyl group it may be for example a straight or branched $C_{1-6}$alkyl group, e.g. a $C_{1-3}$alkyl group such as a methyl or ethyl group.

The linker atom or group represented by $L^1$ in compounds of formula (1) may be any linker atom or group as described above for the linker atom or group $L^3$.

When the group Alk$^1$ is present in compounds of formula (1) as an optionally substituted aliphatic chain it may be an optionally substituted $C_{1-10}$ aliphatic chain. Particular examples include optionally substituted straight or branched chain $C_{1-6}$ alkylene, $C_{2-6}$ alkenylene, or $C_{2-6}$ alkynylene chains.

Particular examples of aliphatic chains represented by Alk$^1$ include optionally substituted —$CH_2$—, —$(CH_2)_2$—, —$CH(CH_3)CH_2$—, —$(CH_2)_2CH_2$—, —$(CH_2)_3CH_2$—, —$CH(CH_3)(CH_2)_2$—, —$CH_2CH(CH_3)CH_2$—, —$C(CH_3CH_2)$, —$CH_2C(CH_3)_2CH_2$—, —$(CH_2)_2C(CH_3)_2CH_2$—, —$(CH_2)_4CH_2$—, —$(CH_2)_5CH_2$—, —CHCH—, —CHCHCH$_2$—, —$CH_2$CHCH—, —CHCHCH$_2$ CH$_2$—, —$CH_2$CHCHCH$_2$—, —$(CH_2)_2$CHCH—, —CC—, —CCCH$_2$—, —$CH_2$CC—, —CCCH$_2$CH$_2$—, —$CH_2$CCCH$_2$—, or —$(CH_2)_2$CCH— groups.

Heteroaliphatic groups represented by the group $R^2$ in the compounds of formula (1) include the aliphatic chains just described for Alk$^1$ but with each containing a further terminal hydrogen atom and additionally containing one, two, three or four heteroatoms or heteroatom-containing groups. Particular heteroatoms or groups include atoms or groups $L^5$ where $L^5$ is as defined above for $L^3$ when $L^3$ is a linker atom or group. Each $L^5$ atom or group may interrupt the aliphatic group, or may be positioned at its terminal carbon atom to connect the group to an adjoining atom or group. Particular examples include optionally substituted —$L^5CH_3$, —$CH_2L^5CH_3$, —$L^5CH_2CH_3$, —$CH_2L^5CH_2CH_3$, —$(CH_2)_2L^5CH_3$, —$(CH_2)_3L^5CH_3$, —$L^5C(CH_3)_3$, and —$(CH_2)_2L^5CH_2CH_3$ groups.

The optional substituents which may be present on aliphatic chains or heteroaliphatic groups represented by Alk$^1$ and $R^2$ respectively include one, two, three or more substituents where each substituent may be the same or different and is selected from halogen atoms, e.g. fluorine, chlorine, bromine or iodine atoms, or —OH, —$CO_2H$, —$CO_2R^9$, where $R^9$ is an optionally substituted straight or branched $C_{1-6}$alkyl group or $C_{3-8}$cycloalkyl group as defined above for $R^4$, —CONHR$^9$, —CON(R$^9$)$_2$, —COR$^9$ e.g. —COCH$_3$, $C_{1-6}$alkoxy, e.g. methoxy or ethoxy, thiol, —S(O)R$^9$, —S(O)$_2$ R$^9$, $C_{1-6}$alkylthio e.g. methylthio or ethylthio, amino or substituted amino groups. Substituted amino groups include —NHR$^9$ and —N(R$^9$)$_2$ groups. Where two R$^9$ groups are present in any of the above substituents these may be the same or different.

Optionally substituted cycloaliphatic groups represented by the group $R^2$ in compounds of the invention include optionally substituted $C_{3-10}$ cycloaliphatic groups. Particular examples include optionally substituted $C_{3-10}$ cycloalkyl, e.g. $C_{3-7}$ cycloalkyl or $C_{3-10}$ cycloalkenyl, e.g $C_{3-7}$ cycloalkenyl groups.

Optionally substituted heterocycloaliphatic groups represented by the group $R^2$ include optionally substituted $C_{3-10}$heterocycloaliphatic groups. Particular examples include optionally substituted $C_{3-10}$heterocycloalkyl, e.g. $C_{3-7}$ heterocycloalkyl, or $C_{3-10}$heterocycloalkenyl, e.g. $C_{3-7}$ hetercycloalkenyl groups, each of said groups containing one, two, three or four heteroatoms or heteroatom-containing groups $L^5$ as defined above.

Optionally substituted polycycloaliphatic groups represented by the group $R^2$ include optionally substitued $C_{7-10}$ bi- or tricycloalkyl or $C_{7-10}$bi- or tricycloalkenyl groups. Optionally substituted heteropolycycloaliphatic groups represented by the group $R^2$ include the optionally substituted polycycloalkyl groups just described, but with each group additionally containing one, two, three or four $L^5$ atoms or groups.

Particular examples of cycloaliphatic, polycycloaliphatic, heterocycloaliphatic and heteropolycycloaliphatic groups represented by the group $R^2$ include optionally substituted cyclopropyl, cyclobutyl, cyclopentyl, cyclohexyl, cycloheptyl, 2-cyclobuten-1-yl, 2-cyclopenten-1-yl, 3-cyclo-penten-1-yl, adamantyl, norbornyl, norbornenyl, tetrahydrofuranyl, pyrroline, e.g. 2- or 3-pyrrolinyl, pyrrolidinyl, pyrrolidinone, oxazolidinyl, oxazolidinone, dioxolanyl, e.g. 1,3-dioxolanyl, imidazolinyl, e.g.

2-imidazolinyl, imidazolidinyl, pyrazolinyl, e.g. 2-pyrazolinyl, pyrazolidinyl, pyranyl, e.g. 2- or 4-pyranyl, piperidinyl, homopiperidinyl, heptamethyleneiminyl, piperidinone, 1,4-dioxanyl, morpholinyl, morpholinone, 1,4-dithianyl, thiomorpholinyl, piperazinyl, homopiperazinyl, 1,3,5-trithianyl, oxazinyl, e.g. 2H-1,3-, 6H-1,3-, 6H-1,2-, 2H-1,2- or 4H-1,4-oxazinyl, 1,2,5-oxathiazinyl, isoxazinyl, e.g. o- or p-isoxazinyl, oxathiazinyl, e.g. 1,2,5 or 1,2,6-oxathiazinyl, or 1,3,5,-oxadiazinyl groups.

The optional substituents which may be present on the cycloaliphatic, polycycloaliphatic, heterocycloaliphatic or heteropolycycloaliphatic groups represented by the group $R^2$ include one, two, three or more substituents each selected from halogen atoms, e.g. fluorine, chlorine, bromine or iodine atoms, or $C_{1-6}$alkyl, e.g. methyl or ethyl, halo$C_{1-6}$alkyl, e.g. halomethyl or haloethyl such as difluoromethyl or trifluoromethyl, optionally substituted by hydroxyl, e.g. —C(OH)(CF$_3$)$_2$, $C_{1-6}$alkoxy, e.g. methoxy or ethoxy, halo$C_{1-6}$alkoxy, e.g. halomethoxy or haloethoxy such as difluoromethoxy or trifluoromethoxy, thiol, $C_{1-6}$alkylthio e.g. methylthio or ethylthio, or —(Alk$^4$)$_v$R$^{10}$ groups in which Alk$^4$ is a straight or branched $C_{1-3}$alkylene chain, v is zero or an integer 1 and $R^{10}$ is a —OH, —SH, —N(R$^{11}$)$_2$, (in which $R^{11}$ is an atom or group as defined herein for $R^8$), —CN, —CO$_2$R$^{11}$, —NO$_2$, —CON(R$^{11}$)$_2$, —CSN(R$^{11}$)$_2$, —COR$^{11}$, —CSN(R$^{11}$)$_2$, —N(R$^{11}$)COR$^{11}$, —N(R$^{11}$)CSR$^{11}$, —SO$_2$N(R$^{11}$)$_2$, —N(R$^{11}$)SO$_2$R$^{11}$, —N(R$^{11}$)CON(R$^{11}$)$_2$, —N(R$^{11}$)CSN(R$^{11}$), —N(R$^{11}$)SO$_2$N(R$^{11}$)$_2$ or optionally substituted phenyl group. Where two $R^{11}$ atoms or groups are present in these substituents these may be the same or different. Additionally, when two $R^{11}$ groups are present as optionally substituted $C_{1-6}$alkyl groups these groups may be joined together with the atoms to which they are attached to form a heterocyclic ring. Such heterocyclic rings may be optionally interrupted by a further heteroatom selected from —O—, —S— or —N(R$^{11}$)—. Particular examples of such heterocyclic rings include piperidinyl, morpholinyl, thiomorpholinyl, pyrrolidinyl, imidazolidinyl and piperazinyl rings. Optionally substituted phenyl groups represented by $R^{10}$ include phenyl substituted by one, two or three of the $R^{13}$ groups described below.

Particular examples of Alk$^4$ chains include —CH$_2$—, —CH$_2$CH$_2$—, —CH$_2$CH$_2$CH$_2$— and —CH(CH$_3$)CH$_2$— chains.

Additionally, when the group $R^2$ is a heterocycloaliphatic group containing one or more nitrogen atoms each nitrogen atom may be optionally substituted by a group —(L$^6$)$_p$(Alk$^5$)$_q$R$^{12}$ in which L$^6$ is —C(O)—, —C(O)O—, —C(S)—, —S(O)$_2$—, —CON(R$^{11}$)—, —CSN(R$^{11}$)— or SO$_2$N(R$^{11}$)—; p is zero or an integer 1; Alk$^5$ is an optionally substituted aliphatic or heteroaliphatic chain; q is zero or an integer 1; and $R^{12}$ is a hydrogen atom or an optionally substituted cycloaliphatic, heterocycloaliphatic, polycycloaliphatic, polyheterocycloaliphatic, aromatic or heteroaromatic group.

Optionally substituted aliphatic or heteroaliphatic chains represented by Alk$^5$ include those optionally substituted chains described above for Alk$^1$ and $R^2$ respectively where in the case of $R^2$ a terminal hydrogen atom is replaced by a bond.

Cycloaliphatic, heterocycloaliphatic, polycycloaliphatic or heteropolycycloaliphatic groups represented by $R^{12}$ include those groups just described for the group $R^2$. Optional substituents which may be present on these groups include those described above in relation to Alk$^1$ aliphatic chains.

Aromatic and heteroaromatic groups represented by $R^{12}$ include those groups described hereinafter for the group $R^2$. Optional substituents which may be present on these groups include those described in relation to $R^2$ aromatic groups.

Optionally substituted aromatic groups represented by $R^2$ when present in the group $R^1$ include for example optionally substituted monocyclic or bicyclic fused ring $C_{6-12}$ aromatic groups, such as phenyl, 1- or 2-naphthyl, 1- or 2-tetrahydronaphthyl, indanyl or indenyl groups.

Optionally substituted heteroaromatic groups represented by the group $R^2$ include for example optionally substituted $C_{1-9}$ heteroaromatic groups containing for example one, two, three or four heteroatoms selected from oxygen, sulphur or nitrogen atoms. In general, the heteroaromatic groups may be for example monocyclic or bicyclic fused ring heteroaromatic groups. Monocyclic heteroaromatic groups include for example five- or six-membered heteroaromatic groups containing one, two, three or four heteroatoms selected from oxygen, sulphur or nitrogen atoms. Bicyclic heteroaromatic groups include for example eight- to thirteen-membered fused-ring heteroaromatic groups containing one, two or more heteroatoms selected from oxygen, sulphur or nitrogen atoms.

Particular examples of heteroaromatic groups of these types include pyrrolyl, furyl, thienyl, imidazolyl, N—$C_{1-6}$alkylimidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, 1,3,4-thiadiazole, pyridyl, pyrimidinyl, pyridazinyl, pyrazinyl, 1,3,5-triazinyl, 1,2,4-triazinyl, 1,2,3-triazinyl, benzofuryl, [2,3-dihydro]benzofuryl, [2,3-dihydro]benzothienyl, benzothienyl, benzotriazolyl, indolyl, isoindolyl, benzimidazolyl, imidazo[1,2-a]pyridyl, benzothiazolyl, benzoxazolyl, benzisoxazolyl, benzopyranyl, [3,4-dihydro]benzopyranyl, quinazolinyl, quinoxalinyl, naphthyridinyl, pyrido[3,4-b]pyridyl, pyrido[3,2-b]pyridyl, pyrido[4,3-b]pyridyl, quinolinyl, isoquinolinyl, tetrazolyl, 5,6,7,8-tetrahydroquinolinyl, 5,6,7,8-tetrahydroisoquinolinyl, and imidyl, e.g. succinimidyl, phthalimidyl, or naphthalimidyl such as 1,8-naphthalimidyl.

Optional substituents which may be present on the aromatic or heteroaromatic groups represented by the group $R^2$ include one, two, three or more substituents, each selected from an atom or group $R^{13}$ in which $R^{13}$ is —$R^{13a}$ or —Alk$^6$(R$^{13a}$)$_m$, where $R^{13a}$ is a halogen atom, or an amino (—NH$_2$), substituted amino, nitro, cyano, amidino, hydroxyl (—OH), substituted hydroxyl, formyl, carboxyl (—CO$_2$H), esterified carboxyl, thiol (—SH), substituted thiol, —COR$^{14}$ [where $R^{14}$ is an —Alk$^6$(R$^{13a}$)$_m$, cycloaliphatic, heterocycloaliphatic, aryl or heteroaryl group], —CSR$^{14}$, —SO$_3$H, —SOR$^{14}$, —SO$_2$R$^{14}$, —SO$_3$R$^{14}$, —SO$_2$NH$_2$, —SO$_2$NHR$^{14}$, —SO$_2$N(R$^{14}$)$_2$, —CONH$_2$, —CSNH$_2$, —CONHR$^{14}$, —CSNHR$^{14}$, —CON(R$^{14}$)$_2$, —CSN(R$^{14}$)$_2$, —N(R$^{11}$)SO$_2$R$^{14}$, —N(SO$_2$R$^{14}$)$_2$, —N(R$^{11}$)SO$_2$NH$_2$, —N(R$^{11}$)SO$_2$NHR$^{14}$, —N(R$^{11}$)SO$_2$N(R$^{14}$)$_2$, —N(R$^{11}$)COR$^{14}$, —N(R$^{11}$)CONH$_2$, —N(R$^{11}$)CONHR$^{14}$, —N(R$^{11}$)CON(R$^{14}$)$_2$, —N(R$^{11}$)CSNH$_2$, —N(R$^{11}$)CSNHR$^{14}$, —N(R$^{11}$)CSN(R$^{14}$)$_2$, —N(R$^{11}$)CSR$^{14}$, —N(R$^{11}$)C(O)OR$^{14}$, —SO$_2$NHet$^1$ [where —NHet$^1$ is an optionally substituted $C_{5-7}$cyclicamino group optionally containing one or more other —O— or —S— atoms or —N(R$^{11}$)—, —C(O)—, —C(S)—, S(O) or —S(O)$_2$ groups], —CONHet$^1$, —CSNHet$^1$, —N(R$^{11}$)SO$_2$NHet$^1$, —N(R$^{11}$)CONHet$^1$, —N(R$^{11}$)CSNHet$^1$, —SO$_2$N(R$^{11}$)Het$^2$ [where Het$^2$ is an optionally substituted monocyclic $C_{5-7}$carbocyclic group optionally containing one or more —O— or —S— atoms or —N(R$^{11}$)—, —C(O)— or —C(S)— groups], —Het$^2$, —CON(R$^{11}$)Het$^2$, —CSN(R$^{11}$)Het$^2$, —N(R$^{11}$)CON(R$^{11}$)Het$^2$, —N(R$^{11}$)CSN(R$^{11}$)Het$^2$, cycloaliphatic, heterocycloaliphatic, aryl or heteroaryl group; Alk$^6$ is a straight or branched C$_{1-6}$alkylene, C$_{2-6}$alkenylene or C$_{2-6}$alkynylene chain, optionally interrupted by one, two or three —O— or —S— atoms or —S(O)$_n$ [where n is an integer 1 or 2] or —N(R$^{15}$)— groups [where R$^{15}$ is a hydrogen atom or C$_{1-6}$alkyl, e.g. methyl or ethyl group]; and m is zero or an integer 1, 2 or 3. It will be appreciated that when two R$^{11}$ or R$^{14}$ groups are present in one of the above substituents, the R$^{11}$ or R$^{14}$ groups may be the same or different.

When in the group —Alk$^6$(R$^{13a}$)$_m$ m is an integer 1, 2 or 3, it is to be understood that the substituent or substituents R$^{13a}$ may be present on any suitable carbon atom in —Alk$^6$. Where more than one R$^{13a}$ substituent is present these may be the same or different and may be present on the same or different atom in —Alk$^6$. Clearly, when m is zero and no substituent R$^{13a}$ is present the alkylene, alkenylene or alkynylene chain represented by Alk$^6$ becomes an alkyl, alkenyl or alkynyl group.

When R$^{13a}$ is a substituted amino group it may be for example a group —NHR$^{14}$ [where R$^{14}$ is as defined above] or a group —N(R$^{14}$)$_2$ wherein each R$^{14}$ group is the same or different.

When R$^{13a}$ is a halogen atom it may be for example a fluorine, chlorine, bromine, or iodine atom.

When R$^{13a}$ is a substituted hydroxyl or substituted thiol group it may be for example a group —OR$^{14}$ or a —SR$^{14}$ or —SC(=NH)NH$_2$ group respectively.

Esterified carboxyl groups represented by the group R$^{13a}$ include groups of formula —CO$_2$Alk$^7$, wherein Alk$^7$ is a group as defined hereinbefore.

When Alk$^6$ is present in or as a substituent it may be for example a methylene, ethylene, n-propylene, 1-propylene, n-butylene, 1-butylene, s-butylene, t-butylene, ethenylene, 2-propenylene, 2-butenylene, 3-butenylene, ethynylene, 2-propynylene, 2-butynylene or 3-butynylene chain, optionally interrupted by one, two, or three —O— or —S—, atoms or —S(O)—, —S(O)$_2$— or —N(R$^9$)— groups.

Cycloaliphatic or heterocycloaliphatic groups represented by the groups R$^{13a}$ or R$^{14}$ include those optionally substituted C$_{3-10}$cycloaliphatic or C$_{3-10}$ heterocycloaliphatic groups described above for R$^2$.

Aryl or heteroaryl groups represented by the groups R$^{13a}$ or R$^{14}$ include mono- or bicyclic optionally substituted C$_{6-12}$ aromatic or C$_{1-9}$ heteroaromatic groups as described above for the group R$^2$. The aromatic and heteroaromatic groups may be attached to the remainder of the compound of formula (1) by any carbon or hetero e.g. nitrogen atom as appropriate.

When —NHet$^1$ or —Het$^2$ forms part of a substituent R$^{13}$ each may be for example an optionally substituted pyrrolidinyl, pyrazolidinyl, piperazinyl, morpholinyl, thiomorpholinyl, piperidinyl or thiazolidinyl group. Additionally Het$^2$ may represent for example, an optionally substituted cyclopentyl or cyclohexyl group. Optional substituents which may be present on —NHet$^1$ or —Het$^2$ include those R$^7$ substituents described above.

Particularly useful atoms or groups represented by R$^{13}$ include fluorine, chlorine, bromine or iodine atoms, or C$_{1-6}$alkyl, e.g. methyl, ethyl, n-propyl, i-propyl, n-butyl or t-butyl, optionally substituted phenyl, pyridyl, pyrimidinyl, pyrrolyl, furyl, thiazolyl, thienyl, morpholinyl, thiomorpholinyl, piperazinyl, e.g. t-butyloxycarbonylpiperazinyl, pyrrolidinyl, dioxolanyl, dioxanyl, oxazolidinyl, thiazolidinyl, imidazolidinyl or piperidinyl, C$_{1-6}$hydroxyalkyl, e.g. hydroxymethyl or hydroxyethyl, carboxyC$_{1-6}$alkyl, e.g. carboxyethyl, C$_{1-6}$alkylthio e.g. methylthio or ethylthio, carboxyC$_{1-6}$alkylthio, e.g. carboxymethylthio, 2-carboxyethylthio or 3-carboxypropylthio, C$_{1-6}$alkoxy, e.g. methoxy or ethoxy, hydroxyC$_{1-6}$alkoxy, e.g. 2-hydroxyethoxy, optionally substituted phenoxy, pyridyloxy, thiazolyoxy, phenylthio or pyridylthio, C$_{4-7}$cycloalkyl, e.g. cyclobutyl, cyclopentyl, C$_{5-7}$cycloalkoxy, e.g. cyclopentyloxy, haloC$_{1-6}$alkyl, e.g. trifluoromethyl, haloC$_{1-6}$alkoxy, e.g. trifluoromethoxy, C$_{1-6}$alkylamino, e.g. methylamino, ethylamino or propylamino, C$_{6-12}$arylC$_{1-6}$alkylamino, e.g.benzylamino, 4-fluorobenzylamino or 4-hydroxyphenylethylamino, amino (—NH$_2$), aminoC$_{1-6}$alkyl, e.g. aminomethyl or aminoethyl, C$_{1-6}$dialkylamino, e.g. dimethylamino or diethylamino, aminoC$_{1-6}$alkylamino, e.g. aminoethylamino or aminopropylamino, optionally substituted Het$^1$NC$_{1-6}$alkylamino, e.g. 3-morpholinopropylamino, C$_{1-6}$alkylaminoC$_{1-6}$alkyl, e.g. ethylaminoethyl, C$_{1-6}$dialkylaminoC$_{1-6}$alkyl, e.g. diethylaminoethyl, aminoC$_{1-6}$alkoxy, e.g. aminoethoxy, C$_{1-6}$alkylaminoC$_{1-6}$alkoxy, e.g. methylaminoethoxy, C$_{1-6}$dialkylaminoC$_{1-6}$alkoxy, e.g. dimethylaminoethoxy, diethylaminoethoxy, diisopropylaminoethoxy, or dimethylaminopropoxy, hydroxyC$_{1-6}$alkylamino, e.g. 2-hydroxyethylamino, 3-hydroxypropylamino or 3-hydroxybutylamino, imido, such as phthalimido or naphthalimido, e.g. 1,8-naphthalimido, nitro, cyano, amidino, hydroxyl (—OH), formyl [HC(O)-], carboxyl (—CO$_2$H), —CO$_2$Alk$^7$ [where Alk$^7$ is as defined above], C$_{1-6}$ alkanoyl e.g. acetyl, propyryl or butyryl, optionally substituted benzoyl, thiol (—SH), thioC$_{1-6}$alkyl, e.g. thiomethyl or thioethyl, —SC(=NH) NH$_2$, sulphonyl (—SO$_3$H), —SO$_3$Alk$^7$, C$_{1-6}$alkylsulphinyl, e.g. methylsulphinyl, ethylsulphinyl or propylsulphinyl, C$_{1-6}$alkylsulphonyl, e.g. methylsulphonyl, ethylsulphonyl or propylsulphonyl, aminosulphonyl (—SO$_2$NH$_2$), C$_{1-6}$alkylaminosulphonyl, e.g. methylaminosulphonyl, ethyl-aminosulphonyl or propylaminosulphonyl C$_{1-6}$dialkylaminosulphonyl, e.g. dimethylaminosulphonyl or diethylaminosulphonyl, phenylaminosulphonyl, carboxamido (—CONH$_2$), C$_{1-6}$alkylaminocarbonyl, e.g. methylaminocarbonyl, ethylaminocarbonyl or propylaminocarbonyl, C$_{1-6}$dialkylaminocarbonyl, e.g. dimethylaminocarbonyl or diethylaminocarbonyl, aminoC$_{1-6}$alkylaminocarbonyl, e.g. aminoethylaminocarbonyl, C$_{1-6}$alkylaminoC$_{1-6}$alkylaminocarbonyl, e.g. methylaminoethylaminocarbonyl, C$_{1-6}$dialkyl-aminoC$_{1-6}$alkylaminocarbonyl, e.g. diethylaminoethylaminocarbonyl, aminocarbonylamino, C$_{1-6}$alkylaminocarbonylamino, e.g. methylaminocarbonylamino or ethylaminocarbonylamino, C$_{1-6}$dialkylaminocarbonylamino, e.g. dimethylaminocarbonylamino or diethylaminocarbonylamino, C$_{1-6}$alkylaminocabonylC$_{1-6}$alkylamino, e.g. methylaminocarbonylmethylamino, aminothiocarbonylamino, C$_{1-6}$alkylaminothiocarbonylamino, e.g. methylaminothiocarbonylamino or ethylaminothiocarbonylamino, C$_{1-6}$dialkylaminothiocarbonylamino, e.g. dimethylaminothiocarbonylamino or diethylaminothiocarbonylamino, C$_{1-6}$alkylaminothiocarbonylC$_{1-6}$alkylamino, e.g. ethylaminothiocarbonylmethylamino, —CONHC(=NH) NH$_2$, C$_{1-6}$alkylsulphonylamino, e.g. methylsulphonylamino or ethylsulphonylamino, haloC$_{1-6}$alkylsulphonylamino, e.g. trifluoromethylsulphonylamino, C$_{1-6}$dialkylsulphonylamino, e.g. dimethylsulphonylamino or diethylsulphonylamino, optionally substituted phenylsulphonylamino, aminosulphonylamino (—NHSO$_2$NH$_2$), C$_{1-6}$alkylaminosulphonylamino, e.g. methylaminosulphonylamino or ethylaminosulphonylamino, C$_{1-6}$dialkylaminosulphonylamino, e.g. dimethylaminosulphonylamino or diethylaminosulphonylamino, optionally substituted morpholinesulphonylamino or morpholinesulphonylC$_{1-6}$alkylamino, optionally substituted phenylaminosulphonylamino, C$_{1-6}$alkanoylamino, e.g. acetylamino, aminoC$_{1-6}$alkanoylamino e.g. aminoacetylamino, C$_{1-6}$dialkylaminoC$_{1-6}$alkanoylamino, e.g. dimethylaminoacetylamino, C$_{1-6}$alkanoylaminoC$_{1-6}$alkyl, e.g. acetylaminomethyl, C$_{1-6}$alkanoylaminoC$_{1-6}$alkylamino, e.g. acetamidoethylamino, C$_{1-6}$alkoxycarbonylamino, e.g. methoxycarbonylamino, ethoxycarbonylamino or t-butoxycarbonylamino or optionally substituted benzyloxy, pyridylmethoxy, thiazolylmethoxy, benzyloxycarbonylamino, benzyloxycarbonylaminoC$_{1-6}$alkyl e.g. benzyloxycarbonylaminoethyl, thiobenzyl, pyridylmethylthio or thiazolylmethylthio groups.

Where desired, two R$^{13}$ substituents may be linked together to form a cyclic group such as a cyclic ether, e.g. a C$_{1-6}$alkylenedioxy group such as methylenedioxy or ethylenedioxy.

It will be appreciated that where two or more R$^{13}$ substituents are present, these need not necessarily be the same atoms and/or groups. In general, the substituent(s) may be present at any available ring position in the aromatic or heteroaromatic group represented by R$^2$.

The presence of certain substituents in the compounds of formula (1) may enable salts of the compounds to be formed. Suitable salts include pharmaceutically acceptable salts, for example acid addition salts derived from inorganic or organic acids, and salts derived from inorganic and organic bases.

Acid addition salts include hydrochlorides, hydrobromides, hydroiodides, alkylsulphonates, e.g. methanesulphonates, ethanesulphonates, or isothionates, arylsulphonates, e.g. p-toluenesulphonates, besylates or napsylates, phosphates, sulphates, hydrogen sulphates, acetates, trifluoroacetates, propionates, citrates, maleates, fumarates, malonates, succinates, lactates, oxalates, tartrates and benzoates.

Salts derived from inorganic or organic bases include alkali metal salts such as sodium or potassium salts, alkaline earth metal salts such as magnesium or calcium salts, and organic amine salts such as morpholine, piperidine, dimethylamine or diethylamine salts.

Particularly useful salts of compounds according to the invention include pharmaceutically acceptable salts, especially acid addition pharmaceutically acceptable salts.

A particularly useful group of compounds according to the invention has the formula (2a):

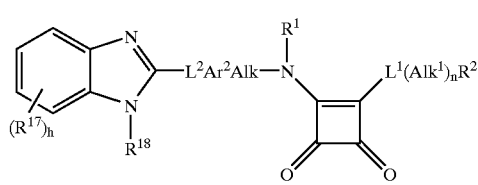

(2a)

wherein R$^{17}$ is an atom or group R$^{16}$ as previously generally and particularly defined, h is the integer g-1 where g is the integer 1, 2, 3 or 4 and R$^{18}$ is a hydrogen atom or an atom or group R$^{16}$; L$^1$, L$^2$, Ar$^2$, Alk, R$^1$, n and R$^2$ are as defined for formula (1); and the salts, solvates, hydrates and N-oxides thereof.

Particularly useful R$^{17}$ substituents when present in compounds of formula (2a) include halogen atoms, especially fluorine or chlorine atoms, or straight or branched C$_{1-6}$alkyl especially methyl, ethyl, propyl or isopropyl, haloC$_{1-6}$alkyl especially halomethyl, most especially —CF$_3$ or —CHF$_2$ C$_{1-6}$alkoxy especially methoxy or ethoxy, haloC$_{1-6}$alkoxy especially halomethoxy, most especially —OCF$_3$, or —OCHF$_2$, —SR$^5$ especially methylthio or ethylthio, —CN, —CO$_2$Alk$^3$, especially —CO$_2$CH$_3$, —NO$_2$, amino (—NH$_2$), substituted amino (—NR$^5$R$^6$), especially —N(CH$_3$)$_2$, —N(R$^5$)COCH$_3$, especially —NHCOCH$_3$ and —COR$^5$, especially —COCH$_3$ groups.

In one preferred class of compounds of formula (2a) h is zero.

In another preferred class of compounds of formula (2a) h is the integer 1 or 2 and each R$^{17}$ is independently chosen from a hydrogen, fluorine or chlorine atom or a C$_{1-6}$alkyl especially methyl or ethyl, —N(CH$_3$)$_2$, —CN, —CF$_3$, methoxy or —OCF$_3$ group.

In another preferred class of compounds of formula (2a) R$^{18}$ is a hydrogen atom.

In another preferred class of compounds of formula (2a) R$^{18}$ is a straight or branched C$_{1-6}$alkyl group, especially a methyl, ethyl, propyl or isopropyl group.

Another particularly useful group of compounds according to the invention has the formula (2b):

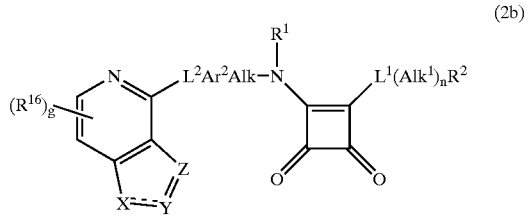

(2b)

wherein R$^{16}$ is a hydrogen atom or an atom or group —L$^3$(Alk$^2$)$_t$L$^4$(R$^4$)$_u$ in which L$^3$, Alk$^2$, t, L$^4$, R$^4$, and u are as previously generally and particularly defined;

X, Y, Z, the broken line ( - - - ), g, L$^1$, L$^2$, Ar$^2$, Alk, R$^1$, Alk$^1$, n and R$^2$ are as defined previously;

and the salts, solvates, hydrates and N-oxides thereof.

In one preferred class of compounds of formulae (1) and (2b) X is an O or S atom and Y and Z are each a CH group, a single bond joins X and Y and a double bond joins Y and Z.

In another preferred class of compounds of formulae (1) and (2b) Z is an O or S atom and X and Y are each a CH group, a single bond joins Y and Z and a double bond joins X and Y.

Particularly useful R$^{16}$ substituents when present in compounds of formula (2) include halogen atoms, especially fluorine or chlorine atoms, or straight or branched C$_{1-6}$alkyl especially methyl, ethyl, propyl or isopropyl, C$_{3-8}$cycloalkyl especially cyclopropyl, cyclobutyl, cyclopentyl or cyclohexyl, haloC$_{1-6}$alkyl especially halomethyl, most especially —CF$_3$ or —CHF$_2$ C$_{1-6}$alkoxy especially methoxy or ethoxy, haloC$_{1-6}$alkoxy especially halomethoxy, most especially —OCF$_3$, or —OCHF$_2$, —SR$^5$ especially methylthio or ethylthio, —CN, —CO$_2$Alk$^3$, especially —CO$_2$CH$_3$, —NO$_2$, amino (—NH$_2$), substituted amino (—NR$^5$R$^6$), and —N(R$^5$)COCH$_3$, especially —NHCOCH$_3$ and —COR$^5$, especially —COCH$_3$ groups.

Alk in compounds of the invention is preferably:

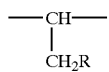

or; especially, —CH$_2$CH(R)—.

In one prefered class of compounds of formulae (1), (2a) and (2b) R is a —CO$_2$H group.

In another prefered class of compounds of formulae (1), (2a) and (2b) R is an esterified carboxyl group of formula —CO$_2$Alk$^7$. In this class of compound Alk$^7$ is preferably a C$_{1-8}$alkyl group, especially a methyl, ethyl, propyl or 1-propyl group, an optionally substituted C$_{6-10}$aryl group, especially a phenyl group, an optionally substituted C$_{6-10}$arylC$_{1-6}$alkyl group, especially a benzyl group, a C$_{3-8}$heterocycloalkylC$_{1-6}$alkyl group, especially a morpholinyl-N-ethyl group or a C$_{1-6}$alkyloxyC$_{1-6}$alkyl group, especially a methyloxyethyl group. Especially preferred esterified carboxyl groups include —CO$_2$CH$_2$CH$_3$, —CO$_2$CH$_2$CH$_2$CH$_3$ and —CO$_2$CH(CH$_3$)$_2$ groups.

In general in compounds of formulae (1), (2a) and (2b) R$^1$ is preferably a hydrogen atom.

In general in compounds of formulae (1), (2a) and (2b) L$^2$ is preferably a –O— atom or —N(R$^8$)— group. Especially useful —N(R$^8$)— groups include —NH— and —N(CH$_3$)—, most especially —NH—.

The group Ar$^2$ in compounds of formulae (1), (2a) and (2b) is preferably an optionally substituted phenylene group. Particularly useful groups include optionally substituted 1,4-phenylene groups.

In general in compounds of formulae (1) and (2) when n is zero or the integer 1 the group R$^2$ may especially be an optionally substituted heteroaliphatic, cycloaliphatic, heterocycloaliphatic, aromatic or heteroaromatic group as defined herein. Particularly useful groups of this type include optionally substituted C$_{2-6}$heteroalkyl, particularly C$_{1-3}$alkoxyC$_{1-3}$alkyl, especially methoxypropyl, optionally substituted C$_{3-7}$cycloalkyl, especially optionally substituted cyclopropyl, cyclobutyl cyclopentyl or cyclohexyl, optionally substituted C$_{5-7}$heterocycloaliphatic, especially optionally substituted pyrrolidinyl, morpholinyl, thiomorpholinyl, or thiazolidinyl, especially optionally substituted phenyl and optionally substituted C$_{5-7}$heteroaromatic, especially optionally substituted pyridyl and pyrimidinyl groups. Optional substituents on these groups include in particular R$^{13}$ atoms or groups where the group is an aromatic or heteroaromatic group and —(L$^6$)$_p$(Alk$^5$)$_q$R$^{12}$ groups as described earlier where the group is a nitrogen-containing heterocycloaliphatic group such as a pyrrolidinyl or thiazolidinyl group. Particularly useful —(L$^6$)$_p$(Alk$^5$)$_q$R$^{12}$ groups include those in which L$^6$ is a —CO— group. Alk$^5$ in these groups is preferably present (i.e. q is preferably an integer 1) and in particular is a —CH$_2$ chain. Compounds of this type in which R$^{12}$ is a hydrogen atom or an optionally substituted aromatic or heteroaromatic group, especially an optionally substituted phenyl, pyridyl or imidazolyl group are particularly preferred.

In one preferred class of compounds of formulae (1) and (2) L$^1$ is present as a —N(R$^8$)— group. Particularly useful —N(R$^8$)— groups include —NH—, —N(CH$_3$)—, —N(CH$_2$CH$_3$)— and —N(CH$_2$CH$_2$CH$_3$)— groups. In this class of compounds n is preferably the integer 1 and Alk$^1$ is preferably an optionally substituted straight or branched C$_{1-6}$alkylene chain. Particularly useful Alk$^1$ chains include —CH$_2$—, —CH$_2$CH$_2$—, —CH$_2$CH$_2$CH$_2$—, —CH(CH$_3$)CH$_2$— and —C(CH$_3$)$_2$CH$_2$—. R$^2$ in this class of compounds is preferably a hydrogen atom.

In another preferred class of compounds of formulae (1) and (2) L$^1$ is a covalent bond, n is the integer (1) and Alk$^1$ is an optionally substituted straight or branched C$_{1-6}$alkylene chain. Particularly useful Alk$^1$ chains include —CH$_2$—, —CH$_2$CH$_2$—, —CH$_2$CH$_2$CH$_2$—, —CH(CH$_3$)CH$_2$— and especially —C(CH$_3$)$_2$CH$_2$— chains. R$^2$ in this class of compounds is preferably a hydrogen atom. A most especially useful optionally substituted Alk$^1$R$^2$ group is —C(CH$_3$)$_3$.

In another preferred class of compounds of formulae (1) and (2), L$^1$ is a covalent bond, n is zero and R$^2$ is an optionally substituted C$_{5-7}$heterocycloaliphatic group. Especially useful C$_{5-7}$heterocycloaliphatic groups include optionally substituted piperidinyl, homopiperidinyl, heptamethyleneiminyl, pyrrolidinyl, piperazinyl, homopiperazinyl, morpholinyl and thiomorpholinyl groups. Most preferred C$_{5-7}$heterocycloaliphatic groups are those linked via a ring nitrogen atom to the remainder of the compound of formulae (1) or (2). Most especially useful C$_{5-7}$ heterocycloaliphatic groups include optionally substituted pyrolidin-1-yl, piperidin-1-yl and homopiperidin-1-yl groups. Especially useful optional substituents on these C$_{5-7}$heterocycloaliphatic groups include optionally substituted C$_{1-6}$alkyl groups, especially methyl, ethyl and 1-propyl groups. Most preferred optionally substituted C$_{5-7}$heterocycloaliphatic groups include 2-methylpyrrolidin-1-yl, cis and trans 2,5-dimethylpyrrolidin-1-yl, 2-methylpiperidin-1-yl, cis and trans 2,6-dimethylpiperidin-1-yl, homopiperidin-1-yl, 2-methylhomopiperidin-1-yl and cis and trans 2,7-dimethylhomopiperidin-1-yl groups.

Particularly useful compounds of the invention include:

S-2-{[2-Dipropylamino)-3,4-dioxo-1-cyclobutenyl]amino}-3-{4-[(1-methylbenzimidazol-2-yl)amino]phenyl}propanoic acid;

S-2-{[2-Dipropylamino)-3,4-dioxo-1-cyclobutenyl]amino}-3-{4-[(1-methylbenzimidazol-2-yl)amino]phenyl}propanoic acid;

S-2-{[2-(2-Methylpiperidin-1-yl)-3,4-dioxo-1-cyclobutenyl]amino}-3-{4-[(1-methylbenzimidazol-2-yl)amino]phenyl}propanoic acid;

(S)-3-[4-(Thiephen[2,3-d]pyrimidin-4-ylamino)phenyl]2-(2-(diethylamino-3,4-dioxocyclobut-1-enylamino) propanoic acid;

and the salts, solvates, hydrates, N-oxides and carboxylic acid esters, particularly the methyl, ethyl, propyl and 1-propyl esters thereof.

Compounds according to the inventions are potent and selective inhibitors of α4 integrins and have advantageous clearance properties, especially those copounds where R is a carboxylic acid ester or amide. The ability of the compounds to act in this way may be simply determined by employing tests such as those described in the Examples hereinafter.

The compounds are of use in modulating cell adhesion and in particular are of use in the prophylaxis and treatment of diseases or disorders involving inflammation in which the extravasation of leukocytes plays a role and the invention extends to such a use and to the use of the compounds for the manufacture of a medicament for treating such diseases or disorders.

Diseases or disorders of this type include inflammatory arthritis such as rheumatoid arthritis vasculitis or polydermatomyositis, multiple sclerosis, allograft rejection, diabetes, inflammatory dermatoses such as psoriasis or dermatitis, asthma and inflammatory bowel disease.

For the prophylaxis or treatment of disease the compounds according to the invention may be administered as pharmaceutical compositions, and according to a further aspect of the invention we provide a pharmaceutical composition which comprises a compound of formula (1) together with one or more pharmaceutically acceptable carriers, excipients or diluents.

Pharmaceutical compositions according to the invention may take a form suitable for oral, buccal, parenteral, nasal, topical or rectal administration, or a form suitable for administration by inhalation or insufflation.

For oral administration, the pharmaceutical compositions may take the form of, for example, tablets, lozenges or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium hydrogen phosphate); lubricants (e.g. magnesium stearate, talc or silica); disintegrants (e.g. potato starch or sodium glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents, emulsifying agents, non-aqueous vehicles and preservatives. The preparations may also contain buffer salts, flavouring, colouring and sweetening agents as appropriate.

Preparations for oral administration may be suitably formulated to give controlled release of the active compound.

For buccal administration the compositions may take the form of tablets or lozenges formulated in conventional manner.

The compounds for formula (1) may be formulated for parenteral administration by injection e.g. by bolus injection or infusion. Formulations for injection may be presented in unit dosage form, e.g. in glass ampoule or multi dose containers, e.g. glass vials. The compositions for injection may take such forms as suspensions, solutions or emulsions in oily or aqueous vehicles, and may contain formulatory agents such as suspending, stabilising, preserving and/or dispersing agents. Alternatively, the active ingredient may be in powder form for constitution with a suitable vehicle, e.g. sterile pyrogen-free water, before use. For particle mediated administration the compounds of formula (1) may be coated on particles such as microscopic gold particles.

In addition to the formulations described above, the compounds of formula (1) may also be formulated as a depot preparation. Such long acting formulations may be administered by implantation or by intramuscular injection.

For nasal administration or administration by inhalation, the compounds for use according to the present invention are conveniently delivered in the form of an aerosol spray presentation for pressurised packs or a nebuliser, with the use of suitable propellant, e.g. dichlorodifluoromethane, trichlorofluoromethane, dichlorotetrafluoroethane, carbon dioxide or other suitable gas or mixture of gases.

For vaginal or rectal administration the compounds of formula (1) may be formulated as a suppository. These formulations may be prepared by mixing the active ingredient with a suitable non-irritating excipient which is a solid at room temperature but liquid at the body temperature. Such materials include for example cocoa butter and polyethylene glycols.

The compositions may, if desired, be presented in a pack or dispenser device which may contain one or more unit dosage forms containing the active ingredient. The pack or dispensing device may be accompanied by instructions for administration.

The quantity of a compound of the invention required for the prophylaxis or treatment of a particular condition will vary depending on the compound chosen, and the condition of the patient to be treated. In general, however, daily dosages may range from around 100 ng/kg to 100 mg/kg e.g. around 0.01 mg/kg to 40 mg/kg body weight for oral or buccal administration, from around 10 ng/kg to 50 mg/kg body weight for parenteral administration and around 0.05 mg to around 1000 mg e.g. around 0.5 mg to around 1000 mg for nasal administration or administration by inhalation or insufflation.

The compounds of the invention may be prepared by a number of processes as generally described below and more specifically in the Examples hereinafter. In the following process description, the symbols $Ar^2$, Alk, $R^1$, $R^2$, $L^1$, $L^2$, $Alk^1$ and n when used in the formulae depicted are to be understood to represent those groups described above in relation to formula (1) unless otherwise indicated. In the reactions described below, it may be necessary to protect reactive functional groups, for example hydroxy, amino, thio or carboxy groups, where these are desired in the final product, to avoid their unwanted participation in the reactions. Conventional protecting groups may be used in accordance with standard practice [see, for example, Green, T. W. in "Protective Groups in Organic Synthesis", John Wiley and Sons, 1991]. In some instances, deprotection may be the final step in the synthesis of a compound of formula (1) and the processes according to the invention described hereinafter are to be understood to extend to such removal of protecting groups. For convenience the processes described below all refer to a preparation of a compound of formula (1) but clearly the description applies equally to the preparation of compounds of formula (2).

Thus according to a further aspect of the invention, a compound of formula (1) in which R is a —$CO_2H$ group may be obtained by hydrolysis of an ester of formula (3):

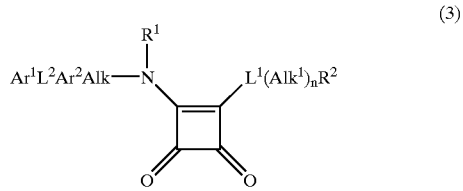

(3)

where $Ar^1$ represents a bicyclic fused-ring heteroaromatic group as previously generally and particularly described; and Alk represents a group

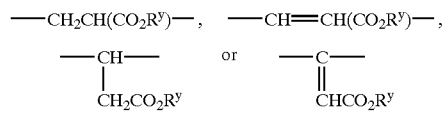

[where $R^y$ is an alkyl group for example a $C_{1-6}$alkyl group]

The hydrolysis may be performed using either an acid or a base depending on the nature of $R^y$, for example an organic acid such as trifluoroacetic acid or an inorganic base such as lithium, sodium or potassium hydroxide optionally in an aqueous organic solvent such as an amide e.g. a substituted amide such as dimethylformamide, an ether e.g. a cyclic ether such as tetrahydrofuran or dioxane or an alcohol e.g. methanol at a temperature from ambient to the reflux temperature. Where desired, mixtures of such solvents may be used.

According to a further aspect of the invention a compound of formula (1) may be prepared by displacement of a leaving group from a compound of formula (4):

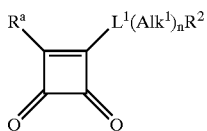
(4)

where $R^a$ is a leaving group, with an amine $Ar^1L^2Ar^2AlkN(R^1)H$ or a salt thereof. Suitable leaving groups represented by $R^a$ include halogen atoms, especially chlorine and bromine atoms, or alkoxy, e.g. methoxy, ethoxy or isopropoxy, aryloxy, e.g. dinitrophenyloxy, or aralkoxy, e.g. benzyloxy, groups.

The reaction may be performed in an inert solvent or mixture of solvents, for example a substituted amide such as dimethylformamide, an alcohol such as ethanol and/or a halogenated hydrocarbon such as dichloromethane, at a temperature from 0° C. to the reflux temperature. Where necessary, for example when a salt of an amine $Ar^1L^2Ar^2AlkN(R^1)H$ is used, an organic base such as diisopropylethylamine can be added.

Any carboxylic acid group present in the intermediate of formula (4) or the amine $Ar^1L^2Ar^2AlkN(R^1)H$ may need to be protected during the displacement reaction, for example as an ethyl ester. The desired acid may then be obtained through subsequent hydrolysis, for example as particularly described above and generally described below.

It will be appreciated that the displacement reaction may also be performed on a compound of formula (5):

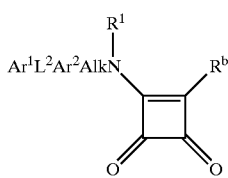
(5)

where $R^b$ is a leaving group as defined for $R^a$ using an intermediate $R^2(Alk^1)_nL^1H$ where $—L^1H$ is a functional group such as an amine ($—NH_2$) using the reaction conditions just described.

It will be further appreciated that when $L^1$ is a covalent bond the displacement reaction may be performed on a compound of formula (5) using an organometallic intermediate of formula $R^2(Alk^1)_nM$ [where M represents a metal such as Li or MgHal, where Hal is a halogen atom such as a chlorine, bromine or iodine atom].

The reaction may be performed in an inert solvent such as an ether e.g. a cyclic ether such as tetrahydrofuran at a temperature from about −78° C. to ambient temperature.

Where desired the displacement reaction may also be performed on an intermediate of formulae (4) or (5), $Ar^1L^2Ar^2AlkN(R^1)H$ or $R^2(Alk^1)_nL^1H$ which is linked, for example via its $Ar^1$ or $R^2$ group, to a solid support, such as a polystyrene resin. After the reaction the desired compound of formula (1) may be displaced from the support by any convenient method, depending on the original linkage chosen.

Intermediates of formulae (4) and (5) are either readily available or may be prepared from an intermediate of formula (6):

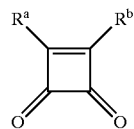
(6)

where $R^a$ and $R^b$ are as previously defined and an amine $Ar^1L^2Ar^2AlkN(R^1)H$ or $R^2(Alk^1)_nL^1H$ or organometallic $R^2(Alk^1)_nM$ by displacement as just described for the preparation of compounds of formula (1).

Intermediates of formulae $Ar^1L^2Ar^2AlkN(R^1)H$, $R^2(Alk^1)_nL^1H$ and $R^2(Alk^1)_nM$ may be obtained from simpler, known compounds by one or more standard synthetic methods employing substitution, oxidation, reduction or cleavage reactions. Particular substitution approaches include conventional alkylation, arylation, heteroarylation, acylation, thioacylation, halogenation, sulphonylation, nitration, formylation and coupling procedures. It will be appreciated that these methods may also be used to obtain or modify other compounds of formulae (1) and (2) where appropriate functional groups exist in these compounds. Thus such intermediates may be prepared by methods known to those skilled in the art following procedures set forth in such references as Rodd's Chemisty of Carbon Compounds, Volumes 1–15 and Supplementals (Elsevier Science Publishers, 1989); Fieser and Fieser's Reagents for Organic Synethesis, Voumes 1–19 (John Wiley & Sons, 1999); Comprehensive Heterocyclic Chemistry, Ed. Kartitzky et al, Volumes 1–8, 1984 and Volumes 1–11, 1994 (Pergamon); Comprehensive Organic Functional Group Transformations, Ed. Trost & Flemming, Volumes 1–8, (Pergamon, 1991); Encyclopedia of Reagents for Organic Synethesis Ed. Paquette, Volumes 1–9 (John Wiley & Sons, 1995); Larock's Comprehensive Organic Transformations (VCH Publishers Inc., 1989) and March's Advanced Organic Chemistry (John Wiley & Sons, 1992).

Thus compounds of the invention and intermediates thereto may be prepared by alkylation, arylation or heteroarylation. For example, compounds containing a $—L^1H$ or $—L^2H$ group (where $L^1$ and $L^2$ is each a linker atom or group) may be treated with a coupling agent $R^2(Alk^1)_nX^1$ or $Ar^1X^1$ respectively in which $X^1$ is a leaving atom or group such as a halogen atom, e.g. a fluorine, bromine, iodine or chlorine atom or a sulphonyloxy group such as an alkylsulphonyloxy, e.g. trifluoromethylsulphonyloxy or arylsulphonyloxy, e.g. p-toluene-sulphonyloxy group.

The reaction may be carried out in the presence of a base such as a carbonate, e.g. caesium or potassium carbonate, an alkoxide, e.g. potassium t-butoxide, or a hydride, e.g. sodium hydride, or an organic amine e.g. triethylamine or N,N-diisopropylethylamine or a cyclic amine, such as N-methylmorpholine or pyridine, in a dipolar aprotic solvent such as an amide, e.g. a substituted amide such as dimethylformamide or an ether, e.g. a cyclic ether such as tetrahydrofuran.

Intermediates of formulae $Ar^1X^1$ and $R^2(Alk^1)_nX^1$ are generally known readily available compounds or may be prepared from known compounds by standard substitution and other synthetic procedures, for example as described herein. Thus for example compounds of formula $Ar^1 X^1$ in which may be prepared from alcohols of formula $Ar^1 OH$ (or their ketotauomers) by reaction with a halogenating agent, for example a phosphorous oxyhalide such as phosphorous oxychloride or thionyl chloride optionally or an inert solvent such as an amide e.g. a substituted amide such as dimethylformamide or a sulfonic acid e.g. methane sulfonic acid at an elevated temperature e.g. 110° C.

In a further example intermediates of formula $Ar^1L^2Ar^2AlkN(R^1)H$ may be obtained by reaction of a compound of formula $Ar^1L^2H$ with a compound of formula $X^1Ar^2AlkN(R^1)H$ under the reaction conditions just described Compounds of formula $Ar^1L^2H$ in which, $L^2$ is a —$N(R^8)$— group, may be prepared from compounds of formula $Ar^1Hal$ [where Hal is a halogen atom such as a chlorine or bromine atom] by treatment with an amine, $(R^8)NH_2$, optionally in the presence of a base such as an inorganic base for example a carbonate e.g. potassium or caesium carbonate or an organic base such as an amine e.g. triethylamine or N-methylmorpholine in an inert solvent such as an amide e.g. a substituted amide such as dimethylformamide or an ether e.g. a cyclic ether such as tetrahydrofuran or a halogenated hydrocarbon such as dichloromethane at a temperature from around ambient to the reflux temperature.

In another example, compounds containing a —$L^1H$ or —$L^2H$ or group as defined above may be functionalised by acylation or thioacylation, for example by reaction with one of the alkylating agents just described but in which $X^1$ is replaced by a —$C(O)X^2$, $C(S)X^2$, —$N(R^8)COX^2$ or —$N(R^8)C(S)X^2$ group in which $X^2$ is a leaving atom or group as described for $X^1$. The reaction may be performed in the presence of a base, such as a hydride, e.g. sodium hydride or an amine, e.g. triethylamine or N-methylmorpholine, in a solvent such as a halogenated hydrocarbon, e.g. dichloromethane or carbon tetrachloride or an amide, e.g. dimethylformamide, at for example ambient temperature. Alternatively, the acylation may be carried out under the same conditions with an acid (for example one of the alkylating agents described above in which $X^1$ is replaced by a —$CO_2H$ group) in the presence of a condensing agent, for example a diimide such as 1-(3-dimethylaminopropyl)-3-ethylcarbodiimide or N,N'-dicyclohexylcarbodiimide, advantageously in the presence of a catalyst such as a N-hydroxy compound e.g. a N-hydroxytriazole such as 1-hydroxybenzotriazole. Alternatively the acid may be reacted with a chloroformate, for example ethylchloroformate, prior to the desired acylation reaction.

In a further example compounds may be obtained by sulphonylation of a compound containing an —OH group by reaction with one of the above alkylating agents but in which $X^1$ is replaced by a —$S(O)Hal$ or —$SO_2Hal$ group [in which Hal is a halogen atom such as chlorine atom] in the presence of a base, for example an inorganic base such as sodium hydride in a solvent such as an amide, e.g. a substituted amide such as dimethylformamide at for example ambient temperature.

In another example, compounds containing a —$L^1H$ or —$L^2H$ group as defined above may be coupled with one of the alkylation agents just described but in which $X^1$ is replaced by an —OH group in a solvent such as tetrahydrofuran in the presence of a phosphine, e.g. triphenylphosphine and an activator such as diethyl, -diisopropyl- or dimethylazodicarboxylate.

In a further example, ester groups —$CO_2R^5$, —$CO_2Alk^3$ or —$CO_2Alk^7$ in the compounds may be converted to the corresponding acid [—$CO_2H$] by acid- or base-catalysed hydrolysis depending on the nature of the groups $R^5$, $Alk^3$ or $Alk^7$. Acid- or base-catalysed hydrolysis may be achieved for example by treatment with an organic or inorganic acid, e.g. trifluoroacetic acid in an aqueous solvent or a mineral acid such as hydrochloric acid in a solvent such as dioxan or an alkali metal hydroxide, e.g. lithium hydroxide in an aqueous alcohol, e.g. aqueous methanol.

In a further example, —$OR^5$ or —$OR^{14}$ groups [where $R^5$ or $R^{14}$ each represents an alkyl group such as methyl group] in compounds of formula (1) may be cleaved to the corresponding alcohol —OH by reaction with boron tribromide in a solvent such as a halogenated hydrocarbon, e.g. dichloromethane at a low temperature, e.g. around –78° C.

Alcohol [—OH] groups may also be obtained by hydrogenation of a corresponding —$OCH_2R^{14}$ group (where $R^{14}$ is an aryl group) using a metal catalyst, for example palladium on a support such as carbon in a solvent such as ethanol in the presence of ammonium formate, cyclohexadiene or hydrogen, from around ambient to the reflux temperature. In another example, —OH groups may be generated from the corresponding ester [$CO_2Alk^5$ or $CO_2R^5$] or aldehyde [—CHO] by reduction, using for example a complex metal hydride such as lithium aluminium hydride or sodium borohydride in a solvent such as methanol.

In another example, alcohol —OH groups in the compounds may be converted to a corresponding —$OR^5$ or —$OR^{14}$ group by coupling with a reagent $R^5OH$ or $R^{14}OH$ in a solvent such as tetrahydrofuran in the presence of a phosphine, e.g. triphenylphosphine and an activator such as diethyl-, diisopropyl-, or dimethylazodicarboxylate.

Aminosulphonylamino [—$NHSO_2NHR^2$] groups in the compounds may be obtained, in another example, by reaction of a corresponding amine [—$NH_2$] with a sulphamide $R^2NHSO_2NH_2$ in the presence of an organic base such as pyridine at an elevated temperature, e.g. the reflux temperature.

In another example compounds containing a —$NHCSR^2$ or —$CSNHR^2$ group may be prepared by treating a corresponding compound containing a —$NHCOR^2$ or —$CONHR^2$ group with a thiation reagent, such as Lawesson's Reagent, in an anhydrous solvent, for example a cyclic ether such as tetrahydrofuran, at an elevated temperature such as the reflux temperature.

In a further example amine (—$NH_2$) groups may be alkylated using a reductive alkylation process employing an aldehyde and a borohydride, for example sodium triacetoxyborohyride or sodium cyanoborohydride, in a solvent such as a halogenated hydrocarbon, e.g. dichloromethane, a ketone such as acetone, or an alcohol, e.g. ethanol, where necessary in the presence of an acid such as acetic acid at around ambient temperature.

In a further example, amine [—$NH_2$] groups in compounds of formula (1) may be obtained by hydrolysis from a corresponding imide by reaction with hydrazine in a solvent such as an alcohol, e.g. ethanol at ambient temperature.

In another example, a nitro [—$NO_2$] group may be reduced to an amine [—$NH_2$], for example by catalytic hydrogenation using for example hydrogen in the presence of a metal catalyst, for example palladium on a support such as carbon in a solvent such as an ether, e.g. tetrahydrofuran or an alcohol e.g. methanol, or by chemical reduction using for example a metal, e.g. tin or iron, in the presence of an acid such as hydrochloric acid.

Aromatic halogen substituents in the compounds may be subjected to halogen-metal exchange with a base, for example a lithium base such as n-butyl or t-butyl lithium, optionally at a low temperature, e.g. around –78° C., in a solvent such as tetrahydrofuran and then quenched with an electrophile to introduce a desired substituent. Thus, for example, a formyl group may be introduced by using dimethylformamide as the electrophile; a thiomethyl group may be introduced by using dimethyldisulphide as the electrophile.

In another example, sulphur atoms in the compounds, for example when present in a linker group $L^1$ or $L^2$ may be oxidised to the corresponding sulphoxide or sulphone using an oxidising agent such as a peroxy acid, e.g. 3-chloroperoxybenzoic acid, in an inert solvent such as a halogenated hydrocarbon, e.g. dichloromethane, at around ambient temperature.

N-oxides of compounds of formula (1) may be prepared for example by oxidation of the corresponding nitrogen base using an oxidising agent such as hydrogen peroxide in the presence of an acid such as acetic acid, at an elevated temperature, for example around 70° C. to 80° C., or alternatively by reaction with a peracid such as peracetic acid in a solvent, e.g. dichloromethane, at ambient temperature.

Salts of compounds of formula (1) may be prepared by reaction of a compound of formula (1) with an appropriate base in a suitable solvent or mixture of solvents e.g. an organic solvent such as an ether e.g. diethylether, or an alcohol, e.g. ethanol using conventional procedures.

Where it is desired to obtain a particular enantiomer of a compound of formula (1) this may be produced from a corresponding mixture of enantiomers using any suitable conventional procedure for resolving enantiomers.

Thus for example diastereomeric derivatives, e.g. salts, may be produced by reaction of a mixture of enantiomers of formula (1) e.g. a racemate, and an appropriate chiral compound, e.g. a chiral base. The diastereomers may then be separated by any convenient means, for example by crystallisation and the desired enantiomer recovered, e.g. by treatment with an acid in the instance where the diastereomer is a salt.

In another resolution process a racemate of formula (1) may be separated using chiral High Performance Liquid Chromatography. Alternatively, if desired a particular enantiomer may be obtained by using an appropriate chiral intermediate in one of the processes described above.

Chromatography, recrystallisation and other conventional separation procedures may also be used with intermediates or final products where it is desired to obtain a particular geometric isomer of the invention.

The following Examples illustrate the invention. All temperatures are in ° C. The following abbreviations are used:

| | |
|---|---|
| NMM - N-methylmorpholine; | EtOAc - ethyl acetate; |
| MeOH - methanol; | BOC - butoxycarbonyl; |
| DCM - dichloromethane | AcOH - acetic acid; |
| DIPEA - diisopropylethylamine; | EtOH - ethanol; |
| Pyr - pyridine; | Ar - aryl; |
| DMSO - dimethylsulphoxide; | iPr - isopropyl; |
| $Et_2O$ - diethylether; | Me - methyl; |
| THF - tetrahydrofuran, | DMF - N,N-dimethylformamide; |
| FMOC - 9-fluorenylmethoxycarbonyl; | TFA - trifluoroactic acid; |
| All NMR's were obtained at 300 mHz. | |

Intermediate 1
s-Chloro-N-methylbenzimidazole

2-Chlorobenzimidazole (5.0 g, 32.7 mmol) was added to an ice cold suspension of sodium hydride (1.44 g, 36.0 mmol, 60% suspension in oil) in DMF (50 ml). After 30 min methyl iodide (2.14 ml, 34.3 mmol) was added and the mxiture stirred at 0° for a further 1 h. Water was then added and the product extracted into DCM, dried and evaporated to give the product as a brown solid (4.6 g, 85%). δH ($CDCl_3$) 7.70 (1H, m), 7.28 (3H, m), and 3.79 (3H, s). m/z ($ES^+$, 70V) 167.5 ($MH^+$).

Intermediate 2
Ethyl S-2-amino-3-{4-[(1-methylbenzimidazol-2-yl)amino]phenyl}propanoate trifluoroacetate salt N-t-butoxycarbonyl-p-amino-L-phenylalanine ethylester (2.0 g, 6.53 mmol) and Intermediate 1 (1.2 g, 7.19 mmol) were dissolved in ethoxyethanol (3 ml) and heated to 100° for 3 h. The reaction mixture was cooled and reduced to dryness in vacuo. The residue was dissolved in DCM (5 ml) and TFA (2.5 ml) added and the solution stirred for 2 h at room temperature. The volatiles were removed in vacuo and the residue azeotroped with heptane. The sticky residue was triturated with diethyl ether to give a solid precipitate which was collected and dried to give the title compound (1.5 g, 51%) δH (DMSO-$d^6$) 7.59 (1H, d, J 7.2 Hz), 7.47 (2H, d, J 8.3 Hz), 7.40–7.22 (5H, m), 4.30 (1H, m), 4.14 (2H, q, J 7.0 Hz), 3.77 (3H, s), 3.17 (1H, dd, J 14.0, 6.0 Hz), 3.06 (1H, dd, J 14.0 and 7.8 Hz) and 1.14 (3H, t, J 7.0 Hz). m/z ($ES^+$, 70V) 339 ($MH^+$).

Intermediate 3
Ethyl S-2-{[2-(isopropoxy)-3,4-dioxo-1-cyclobutenyl]amino}-3-{4-[(1-methylbenzimidazol-2-yl)amino]phenyl}propanoate Intermediate 2 (1.50 g, 3.32 mmol), diisopropylsquarate (0.72 g, 3.65 mmol) and DIPEA (0.87 ml, 4.98 mmol) were added to isopropanol (20 ml) and heated to 60° for 6 h. The mixture was then cooled and the volatiles removed in vacuo. Purification by flash chromatography (silica; 3:2 DCM/EtOAc) gave the title compound as an off white foam (1.3 g), δH (MeOD) 7.45 (1H, m), 7.34 (1H, m), 7.22 (3H, m), 7.10 (2H, m), 5.30 (1H, m), 5.15–4.60 (1H, v br.m), 4.24 (2H, q, J 7.0 Hz), 3.67 (3H, s), 3.30 (1H, m), 2.96 (1H, dd, J 14.0, 10.4 Hz), 1.40 (6H, m) and 1.29 (3H, t, J 7.0 Hz). m/z ($ES^+$, 70V) 477 ($MH^+$).

Intermediate 4
Methyl (S)-3-[4-{(thiophen[2,3-d]pyromidin-4-yl)amino}phenyl]-2-(t-butoxycaronylamino)propanoat A solution of methyl (S)-3-[4-(aminophenyl)-2-(t-butoxycarbonylamino) propanoate (1.01 g, 3.6 mmol), 4-chlorothiophen[2,3-d]pyrimidine (0.61 g, 3.6 mmol) and DIPEA (0.69 ml, 4.0 mmol) in ethoxyethanol (0.8 ml) was heated to 120° under nitrogen for 5 h, then cooled to room temperature. The reaction mixture was dissolved in EtOAc, washed with water, dried ($MgSO_4$) and then concentrated in vacuo. The residue was purified by chromatography (silica; EtOAc/hexane, gradient elution 30–40%) to give the title compound (1.07 g, 72%). δH ($CDCl_3$) 8.61 (1H,s ), 7.59 (2H, d, J 8.4 Hz), 7.35 (1H, d, J 6.0 Hz), 7.14 (4H, m), 5.02 (1H, m), 4.58 (1H, m), 3.73 (3H, s), 3.10 (2H, m), 1.43 (9H, s). m/z ($ES^+$, 70V) 429 ($MH^+$).

EXAMPLE 1

Methyl S-2-{[2-(dipropylamino)-3,4-dioxo-1-cyclobutenyl]amino}-3-[4-[(1-methylbenzimidazol-2-yl)amino]phenyl}propanoate Intermediate 3 (430 mg, 0.91 mmol) was dissolved in MeOH (20 ml) and treated with dipropylamine (187 µl, 1.37 mmol) and heated to 60° overnight. The reaction was cooled and the volatiles removed in vacuo. The residue was purified by flash chromatography (silica; 3:2 DCM/EtOAc) to give the title compound as a white foam (250 mg). δH (MeOD) 7.44 (2H, d, J 8.5 Hz), 7.36 (1H, m), 7.24 (1H, m), 7.20 (2H, d, J 8.5 Hz), 7.10 (2H, m), 5.33 (1H, dd, J 10.3, 4.7 Hz), 3.79 (3H, s), 3.66 (3H, s), 3.49 (4H, br m), 3.35 (1H, dd, J 14.1, 4.7 Hz), 3.03 (1H, dd, J 14.1, 10.3 Hz), 1.59 (4H, m) and 0.88 (6H, t, J 7.3 Hz); m/z ($ES^+$, 70V) 504 ($MH^+$).

The compounds of Examples 2 and 3 were made in a similar manner to Example 1 using the amine indiciated.

EXAMPLE 2

Methyl S-2-{[2-(2,5-dimethylpyrrolidin-1-yl)-3,4-dioxo-cyclobutenyl]amino}-3-{4-[(1-methylbenzimidazol-2-yl) amino]phenyl}propanoate Intermediate 3 treated with 2,5-dimethylpyrrolidine yielded the title compound (310 mg). δH (MeOD) 7.50–7.20 (8H, m), 5.36 (1H, m), 4.22 (2H, m), 3.81 (3H, s), 3.76 (3H, s), 3.43 (1H, m), 3.09 (1H, dd, J 13.6, 10.7 Hz), 2.20 (2H, m), 1.75 (2H, m), 1.34 (3H, d, J 6.5 Hz) and 1.30 (3H, d, J 6.5 Hz); m/z (ES$^+$, 70V) 502 (MH$^+$).

EXAMPLE 3

Methyl S-2-{[2-(2-methylpiperidin-1-yl)-3,4-dioxo-1-cyclobutenyl]amino}-3-{4-[(1-methylbenzimidozol-2-yl) amino]phenyl}propanoate Intermediate 3 treated with 2-methylpiperidine yielded the title compound (200 mg) δH (MeOD) 7.45 (2H, d, J 8.2 Hz), 7.36 (1H, m), 7.22 (3H, m), 7.09 (2H, m), 5.34 (1H, m), 4.46 (1H, m), 3.79 (3H, s), 3.66 (3H, s), 3.33 (1H, m), 3.00 (1H, m), 1.9–1.5 (8H, m) and 1.29 (3H, d, J 6.9 Hz); m/z (ES$^+$, 70V) 502 (MH$^+$).

EXAMPLE 4

S-2-{(2-Dipropylamino)-3,4-dioxo-1-cyclobutenyl]amino}-3-{4-[(1-methylbenzimidazol-2-yl)amino] phenyl}propanoic acid The compound of Example 1 (250 mg, 0.50 mmol) was dissolved in THF (5 ml) and water (5 ml) and lithium hydroxide monohydrate (25 mg, 0.55 mmol) added. The mixture was stirred at room temperature overnight. The THF was removed in vacuo and the remaining aqueous solution acidified to ~pH 6 with 1 M HCl. The product was extracted into DCM, the organic layer dried (Na$_2$SO$_4$) and evaporated. Purification by flash chromatography (silica; 10% MeOH in DCM) gave the title compound as a white solid (207 mg). δH (DMSO-d$^6$, 350K) 7.74 (2H, d, J 8.5 Hz), 7.39 (1H, m), 7.28 (1H, m,) 7.21 (2H, q, J 8.5 Hz), 7.08 (2H, m), 5.09 (1H, m), 3.46 (4H, m), 3.26 (1H, dd, J 14.0, 4.8 Hz), 3.09 (1H, dd, J 14.0, 9.3 Hz), 1.58 (4H, m) and 0.89 (6H, t, J 7.4 Hz); m/z (ES$^+$, 70V) 490 (MH$^+$).

Examples 5 and 6 were made in a similar fashion to Example 4

EXAMPLE 5

S-2-{(2-Dipropylamino)-3,4-dioxo-1-cyclobutenyl]amino}-3-{4-[(1-methylbenzimidazol-2-yl)amino] phenyl}propanoic acid Using the compound of Example 2 yielded the title compound (146 mg) δH (DMSO-d$^6$, 350K) 7.60 (2H, d, J 8.6 Hz), 7.42 (1H, m), 7.31 (1H, m), 7.25 (2H, d, J 8.6 Hz), 7.11 (3H, m), 5.08 (1H, m), 4.40 (0.36H, (trans isomer) m), 4.28 (1.64H, (cis isomer), m), 3.74 (3H, s), 3.28 (1H, dd, J 14.1, 4.8 Hz), 3.14 (1H, dd, J 14.1, 8.9 Hz), 2.17 (2H, m), 1.76 (1.64H (cis isomer) m), 1.62 (0.36H, (trans isomer), m), 1.34 (2.45H, (cis isomer), d, J 6.4 Hz), 1.30 (2.45H (cis isomer), d, J 6.4 Hz), 1.17 (0.55H, (trans isomer), d, J 6.5 Hz) and 1.10 (0.55H, (trans isomer), d, J6.5 Hz); m/z (ES$^+$, 70V) 488 (MH$^+$).

EXAMPLE 6

S-2-{[2-(2-Methylpiperidin-1-yl)-3,4-dioxo-1-cyclobutenyl]amino}-3-{4-[(1-methylbenzimidazol-2-yl) amino]phenyl}propanoic acid Using the compound of Example 3 yielded the title compound (183 mg) δH (DMSO-d$^6$, 350K) 7.70 (2H, d, J 8.5 Hz), 7.55 (1H, m), 7.45 (2H, m), 7.31 (2H, d, J 8.5 Hz), 7.20 (2H, m), 5.22 (1H, m), 4.53 (1H, m), 4.11 (1H, m), 3.78 (3H, s), 3.30–3.15 (2H, m), 1.90–1.50 (8H, m) and 1.30 (3H, t, J 6.8 Hz). m/z (ES$^+$, 70V) 488 (MH$^+$).

EXAMPLE 7

Methyl (S)-3-[4-{(thiophen[2,3-d]pyrimidin-4-yl) amino}phenyl]-2-[(isopropoxy-3,4-dioxocyclobut-1-enyl) amino]propanoate A solution of Intermediate 4 (1.07 g, 2.5 mmol) was stirred with a EtOAc solution of HCl (2.6M, 10 ml) for 1.5 h. The mixture was diluted with EtOAc (75 ml) and NaHCO$_3$ solution added. The organic layer was separated, washed with brine, dried (MgSO$_4$) and concentrated in vacuo. The crude proudct was dissoled in EtOH and 3,4-diisopropoxy-3-cyclobutene-1,2-dione (0.49 g, 2.5 mmol) and 3,4-diisopropoxy-3-cyclobutene-1,2-dione (0.49 g, 2.5 mmol) and DIPEA (0.46 g, 3.8 mmol) added. The reaction was stirred for 16 h then concentrated in vacuo, the residue dissolved in EtOAc, washed with 10% citric acid, NaHCO$_3$ solution and brine, dried (MgSO$_4$) and concentrated in vacuo. The residue was purified by chromatography (silica; DCM/MeOH 95:5) to give the title compound as a pale yellow solid (0.91 g, 60%). δH (CDCl$_3$) 8.60 (1H, s), 7.62 (2H, d, J 8.5 Hz), 7.38 (1H, d, J 6.0 Hz), 7.24–7.13 (4H, m), 5.34 (1H, m), 3.82 (3H, s), 3.22 (2H, m), 1.41 (3H, d, J 6.1 Hz), 1.39 (3H, d, J 6.1 Hz); m/z (ES$^+$, 70V) 467 (MH$^+$).

EXAMPLE 8

Ethyl-(S)-3-[4-(thiophen[2,3-d]pyrimidin-4-ylamino) phenyl]-2-(2-diethylamino-3,4-dioxocyclobut-1-enylamino)propanoate A solution of the compound of Example 7 (0.50 g, 0.11 mmol) in EtOH (8 ml) was treated with diethylamine (0.22 ml, 0.22 mmol) and stirred at 45° for 16 h. The reaction was concentrated in vacuo, the residue dissolved in EtOAc, washed with brine, dried (MgSO$_4$) and concentrated in vacuo. The residue was purified by chromatography (SiO$_2$; DCM/MeOH 9:1) to give the title compound as a yellow foam (0.46 g, 89%). $\delta_H$ (CDCl$_3$) 8.58 (1H, s), 7.64 (2H, d, J 8.5 Hz), 7.42 (1H, s), 7.36 (1H, d, J 5.95 Hz), 7.28 (2H, n r m), 7.15 (2H, d, J 8.51 Hz), 5.38 (1H, br s), 4.24 (2H, dd, J 14.3, 7.17 Hz), 3.62–3.35 (2H, m), 3.3–3.1 (2H, m), 1.30 (3H, t, J 7.18 Hz), 1.26–1.20 (6H, m). m/z (ES$^+$, 70V) 494 (MH$^+$).

EXAMPLE 9

(S)-3-[4-(Thiophen[2,3-d]pyrimidin-4-ylamino)phenyl]2-(2-(diethylamino-3,4-dioxocyclobut-1-enylamino) propanoic acid A solution of the compound of Example 8 (0.45 g, 0.09 mmol) in dioxan (2 ml), MeOH (1 ml) and water (2 ml) was treated with LiOH.H$_2$O (58 mg, 1.35 mmol) and the reaction sitrred for 5 h, acidified with AcOH and concentrated in vacuo. The residue was purified by chromatography (SiO$_2$; DCM/MeOH/AcOH/H$_2$O 200/20/3/1) to give the title compound as a white solid (0.31 g, 68%). δH (DMSO, 390K) 8.52 (1H, s), 7.82 (1H, d, J 6.0 Hz), 7.77 (2H, d, J 8.5 Hz), 7.65 (1H, d, J 6.0 Hz), 7.33 (2H, d, J 8.7 Hz), 5.22 (1H, br s), 3.67–3.57 (4H, m), 3.35 (1H, dd, J 14.2, 5.1 Hz), 3.18 (1H, dd, J 14.2, 9.1 Hz), 1.22 (6H, t, J 7.1 Hz); m/z (ES$^+$, 70V) 466 (MH$^+$).

The following assays can be used to demonstrate the potency and selectivity of the compounds according to the invention. In each of these assays an IC$_{50}$ value was determined for each test compound and represents the concentration of compound necessary to achieve 50% inhibition of cell adhesion where 100%=adhesion assessed in the absence of the test compound and 0%=absorbance in wells that did not receive cells.

$\alpha_4\beta_1$ Integrin-dependent Jurkat Cell Adhesion to VCAM-Ig 96 well NUNC plates were coated with F(ab)$_2$ fragment goat anti-human IgG Fcγ-specific antibody [Jackson 1 mmuno Research 109-006-098: 100 μl at 2 μg/ml in 0.1M NaHCO$_3$, pH 8.4], overnight at 40. The plates were washed (3×) in phosphate-buffered saline (PBS) and then blocked for 1 h in PBS/1% BSA at room temperature on a rocking platform. After washing (3× in PBS) 9 ng/ml of purified 2d VCAM-Ig diluted in PBS/1% BSA was added and the plates left for 60 minutes at room temperature on a rocking platform. The plates were washed (3× in PBS) and the assay then performed at 37° for 30 min in a total volume of 200 μl containing 2.5×10$^5$ Jurkat cells in the presence or absence of titrated test compounds.

Each plate was washed (2×) with medium and the adherent cells were fixed with 100 μl MeOH for 10 minutes followed by another wash. 100 μl 0.25% Rose Bengal (Sigma R4507) in PBS was added for 5 minutes at room temperature and the plates washed (3×) in PBS. 100 μl 50% (v/v) ethanol in PBS was added and the plates left for 60 min after which the absorbance (570 nm) was measured.

$\alpha_4\beta_7$ Integrin-dependent JY Cell Adhesion to MAdCAM-Ig

This assay was performed in the same manner as the $\alpha_4\beta_1$ assay except that MAdCAM-Ig (150 ng/ml) was used in place of 2d VCAM-Ig and a sub-line of the β-lymphoblastoid cell-line JY was used in place of Jurkat cells. The IC$_{50}$ value for each test compound was determined as described in the $\alpha_4\beta_1$ integrin assay.

$\alpha_5\beta_1$ Integrin-dependent K562 Cell Adhesion to Fibronectin 96 well tissue culture plates were coated with human plasma fibronectin (Sigma F0895) at 5 μg/ml in phosphate-buffered saline (PBS) for 2 hr at 37° C. The plates were washed (3× in PBS) and then blocked for 1 h in 100 μl PBS/1% BSA at room temperature on a rocking platform. The blocked plates were washed (3× in PBS) and the assay then performed at 37° C. in a total volume of 200 μl containing 2.5×10$^5$ K562 cells, phorbol-12-myristate-13-acetate at 10 ng/ml, and in the presence or absence of titrated test compounds. Incubation time was 30 minutes. Each plate was fixed and stained as described in the $\alpha_4\beta_1$ assay above.

$\alpha_m\beta_2$-Dependent Human Polymorphonuclear Neutrophils Adhesion to Plastic 96 well tissue culture plates were coated with RPMI 1640/10% FCS for 2 h at 37° C. 2×10$^5$ freshly isolated human venous polymorphonuclear neutrophils (PMN) were added to the wells in a total volume of 200 μl in the presence of long/ml phorbol-12-myristate-13-acetate, and in the presence or absence of test compounds, and incubated for 20 m in at 37° C. followed by 30 min at room temperature. The plates were washed in medium and 100 μl 0.1% (w/v) HMB (hexadecyl trimethyl ammonium bromide, Sigma H5882) in 0.05M potassium phosphate buffer, pH 6.0 added to each well. The plates were then left on a rocker at room temperature for 60 min. Endogenous peroxidase activity was then assessed using tetramethyl benzidine (TMB) as follows: PMN lysate samples mixed with 0.22% H$_2$O$_2$ (Sigma) and 50 μg/ml TMB (Boehringer Mannheim) in 0.1M sodium acetate/citrate buffer, pH 6.0 and absorbance measured at 630 nm.

αIIb/β$_3$-Dependent Human Platelet Aggregation

Human platelet aggregation was assessed using impedance aggregation on the Chronolog Whole Blood Lumiaggregometer. Human platelet-rich plasma (PRP) was obtained by spinning fresh human venous blood anticoagulated with 0.38% (v/v) tri-sodium citrate at 220× g for 10 min and diluted to a cell density of 6×10$^8$/ml in autologous plasma. Cuvettes contained equal volumes of PRP and filtered Tyrode's buffer (g/liter: NaCl 8.0; MgCl$_2$.H$_2$O 0.427; CaCl$_2$ 0.2; KCl 0.2; D-glucose 1.0; NaHCO$_3$ 1.0; NaHPO$_4$.2H$_2$O 0.065). Aggregation was monitored following addition of 2.5 μM ADP (Sigma) in the presence or absence of inhibitors.

In the above assays the preferred compounds of the invention in which R$^1$ is an α4 integrin binding group, such as the compounds of the Examples generally have IC$_{50}$ values in the $\alpha_4\beta_1$ and $\alpha_4\beta_7$ assays of 1 μM and below. In the other assays featuring α integrins of other subgroups the same compounds had IC$_{50}$ values of 50 μM and above thus demonstrating the potency and selectivity of their action against α$_4$ integrins.

The advantageous clearance properties of compounds according to the invention may be demonstrated as follows:

Hepatic clearance, whether metabolic or biliary, can make a substantial contribution to the total plasma clearance of a drug. The total plasma clearance is a principal parameter of the pharmacokinetic properties of a medicine. It has a direct impact on the dose required to achieve effective plama concentrations and has a major impact on the elimination half-life and therefore the dose-interval. Furthermore, high hepatic clearance is an indicator of high first-pass hepatic clearance after oral administration and therefore low oral bioavailability.

Many peptidic and non-peptidic carboxylic acids of therapeutic interest are subject to high hepatic clearance from plasma. Except for drugs which function in the liver, hepatic uptake from blood or plasma is undesirable because it leads to high hepatic clearance if the compound is excreted in bile or metabolised, or if the substance is not cleared from the liver, it may accumulate in the liver and interfere with the normal function of the liver.

The total plasma clearance of a compound according to the invention can be determined as follows:

a small dose of the compound in solution is injected into a vein of a test animal. Blood samples are withdrawn from a blood vessel of the animal at several times after the injection, and the concentration of compound in the bleed or plasma is measured using a suitable assay. The area under the curve (AUCiv) is calculated by non-compartmental methods (for example, the trapezium method) or by pharmacokinetic modelling. The total plasma clearance (CL$_p$) is calculated by dividing the intravenous dose(D$_{iv}$) by the AUC$_{iv}$ for the blood plasma concentration–time course of a drug administered by the intravenous route: CL$_p$=D$_{iv}$÷AUC$_{iv}$ When tested in this manner, compounds according to the invention are not rapidly or extensively extracted by the liver and have low total plasma clearance where low is defined as less than 10 ml/min/kg in the laboratory rat (Sprague Dawley CD). This compares favourably with functionally equivalent integrin binding compounds in which the squaric acid framework of compounds of formula (1) is not present.

We claim:
1. A compound of formula (1):

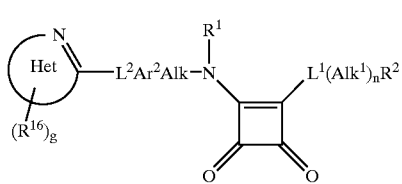

wherein
Het is a bicyclic fused ring heteroaromatic group;
g is zero or the integer 1, 2, 3 or 4;
Each $R^{16}$, which may be the same or different, is an atom or group —$L^3(Alk^2)_tL^4(R^4)_u$,
$L^3$ and $L^4$, which may be the same or different, are each a covalent bond or a linker atom or group —O—, —S—, —C(O)—, —C(O)O—, —OC(O)—, —C(S)—, —S(O)—, —S(O)$_2$—, —N($R^8$)—, —N($R^8$)O—, —N($R^8$)N—, —CON($R$)$^8$)—, —OC(O)N($R^8$)—, —CSN($R^8$)—, —N($R^8$)CO—, —N($R^8$)C(O)O—, —N($R^8$)CS—, —S(O)$_2$N($R^8$)—, —N($R^8$)S(O)$_2$—, —N($R^8$)CON($R^8$)—, —N($R^8$)CSN($R^8$)—, or —N($R^8$)SO$_2$N($R^8$)—,
$R^8$ is a hydrogen atom or an optionally substituted $C_{1-6}$alkyl group,
t is zero or the integer 1,
u is an integer 1, 2 or 3,
$Alk^2$ is an aliphatic or heteroaliphatic chain, and
$R^4$ is a hydrogen or halogen atom or a group selected from an optionally substituted $C_{1-6}$alkyl or $C_{3-8}$ cycloalkyl group, —$OR^5$ (where $R^5$ is a hydrogen atom, an optionally substituted $C_{1-6}$alkyl or $C_{3-8}$ cycloalkyl group), —$SR^5$, —$NR^5R^6$ (where $R^6$ is as just defined for $R^5$ and may be the same or different), —$NO_2$, —CN, —$CO_2R^5$, —$SO_3H$, —$SOR^5$, $SO_2R^5$, —$SO_3R^5$, —$OCO_2R^5$, —$CONR^5R^6$, —$OCONR^5R^6$, —$CSNR^5R^6$, —$COR^5$, —$OCOR^5$, —N($R^5$)$COR^6$, —N($R^5$)$CSR^6$, —$SO_2N(R^5)(R^6)$, —N($R^5$)$SO_2R^6$, —N($R^5$)$CON(R^6)(R^7)$, (where $R^7$ is a hydrogen atom, an optionally substituted $C_{1-6}$alkyl or $C_{3-8}$cycloalkyl group), —N($R^5$)$CSN(R^6)(R^7)$ or —N($R^5$)$SO_2N(R^6)(R^7)$,
provided that when t is zero and each of $L^3$ and $L^4$ is a covalent bond then u is the integer 1 and $R^4$ is other than a hydrogen atom;
$L^2$ is a covalent bond or an atom or group —O—, —S—, —C(O)—, —C(S)—, —S(O)—, —S(O)$_2$—, —N($R^8$)— or —C($R^8$)($R^{8a}$)— (where $R^{8a}$ is an atom or group as defined for $R^8$ and may be the same or different);
$Ar^2$ is an optionally substituted aromatic or heteroaromatic group;
Alk is a chain

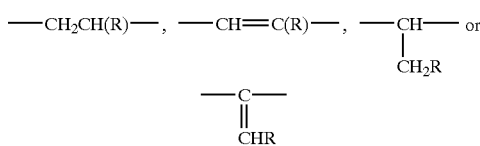

in which R is a carboxylic acid (—$CO_2H$), a carboxylic acid ester, a carboxylic acid amide, or a carboxylic acid biostere;

$R^1$ is a hydrogen atom or a $C_{1-6}$alkyl group;
$L^1$ is a covalent bond or a linker atom or group —O—, —S—, —C(O)—, —C(O)O—, —OC(O)—, —C(S)—, —S(O)—, —S(O)$_2$—, —N($R^8$)—, —N($R^8$)O—, —N($R^8$)N—, —CON($R^8$)—, —OC(O)N($R^8$)—, —CSN($R^8$)—, —N($R^8$)CO—, —N($R^8$)C(O)O—, —N($R^8$)CS—, —S(O)$_2$N($R^8$)—, —N($R^8$)S(O)$_2$—, —N($R^8$)CON($R^8$)—, —N($R^8$)CSN($R^8$)—, or —N($R^8$)SO$_2$N($R^8$)—;
$Alk^1$ is an optionally substituted aliphatic chain;
n is zero or the integer 1;
$R^2$ is a hydrogen atom or an optionally substituted heteroaliphatic, $C_{3-10}$cycloaliphatic, $C_{3-10}$heterocycloaliphatic, $C_{7-10}$polycycloaliphatic, $C_{7-10}$heteropolycycloaliphatic, aromatic or heteroaromatic group, wherein said heteroaliphatic, $C_{3-10}$heterocycloaliphatic, and $C_{7-10}$heteropolycycloaliphatic groups contain one, two, three, or four heteroatoms or heteroatom-containing groups as defined for $L^3$ and $L^4$, which may be the same or different;
provided that Het is not a 2,6-naphthyridin-1-yl, isoquinolin-1-yl, 2,7-naphthyridin-1-yl or quinazolin-4-yl group;
and the salts and N-oxides thereof.
2. A compound according to claim 1 in which Alk is a chain

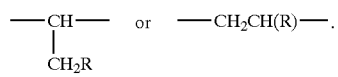

3. A compound according to claim 1 in which R is a carboxylic acid (—$CO_2H$) group.
4. A compound according to claim 1 in which R is an esterified carboxyl group of formula —$CO_2Alk^7$.
5. A compound according to claim 1 in which $R^1$ is a hydrogen atom.
6. A compound according to claim 1 in which $Ar^2$ is an optionally substituted phenylene group.
7. A compound according to claim 1 in which $L^1$ is a —N($R^8$)— group where $R^8$ is a hydrogen atom or an optionally substituted $C_{1-6}$alkyl group.
8. A compound according to claim 7 in which $R^8$ is a methyl, ethyl or n-propyl group.
9. A compound according to claim 1 in which $L^1$ is a covalent bond.
10. A compound according to claim 1 in which n is the integer 1, $Alk^1$ is an optionally substituted straight or branched $C_{1-6}$alkylene chain and $R^2$ is a hydrogen atom.
11. A compound according to claim 10 in which $Alk^1$ is a —$CH_2$—, —$CH_2CH_2$—, —$CH_2CH_2CH_2$—, —$CH(CH_3)CH_2$— or —$C(CH_3)_2CH_2$— chain.
12. A compound according to claim 1 in which $L^1$ is a covalent bond, n is zero and $R^2$ is an optionally substituted $C_{5-7}$heterocycloaliphatic group.
13. A compound according to claim 12 in which $R^2$ is an optionally substituted piperidinyl, homopiperidinyl, heptamethyleneiminyl, pyrrolidinyl, piperazinyl, homopiperazinyl, morpholinyl or thiomorpholinyl group.
14. A compound according to claim 1 in which $L^2$ is an —O— atom or —N($R^8$)— group in which $R^8$ is a hydrogen atom or an optionally substituted $C_{1-6}$alkyl group.

15. A compound according to claim 1 of formula (2a):

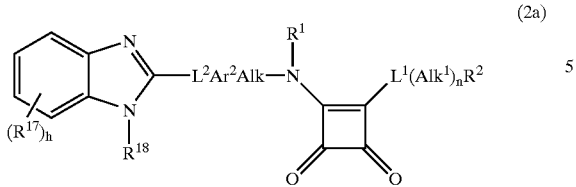

(2a)

wherein:
R$^{17}$ is an atom or group R$^{16}$ as previously defined;
h is zero or the integer 1, 2 or 3;
R$^{18}$ is a hydrogen atom or an atom or group R$^{16}$ as previously defined;
and the salts and N-oxides thereof.

16. A compound according to claim 1 of formula (2b):

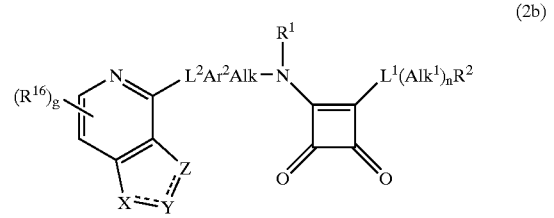

(2b)

wherein:
X, Y and Z is each independently selected from a nitrogen, oxygen or sulphur atom or CH group;
the broken line ( - - - ) represents saturation or unsaturation;
and the salts and N-oxides thereof.

17. A compound according to claim 16 in which X is an O or S atom, Y and Z are each a group CH, a single bond joins X and Y and a double bond joins Y and Z.

18. A compound according to claim 16 in which Z is an O or S atom, X and Y are each a CH group, a single bond joins Y and Z and a double bond joins X and Y.

19. A compound which is:

S-2-{[2-Dipropylamino)-3,4-dioxo-1-cyclobutenyl]amino}-3-{4-[(1-methylbenzimidazol-2-yl)amino]phenyl}propanoic acid;

S-2-{[2-Dipropylamino)-3,4-dioxo-1-cyclobutenyl]amino}-3-{4-[(1-methylbenzimidazol-2-yl)amino]phenyl}propanoic acid;

S-2-{[2-(2-Methylpiperidin-1-yl)-3,4-dioxo-1-cyclobutenyl]amino}-3-{4-[(1-methylbenzimidazol-2-yl)amino]phenyl}propanoic acid;

(S)-3-[4-(Thiophen[2,3-d]pyrimidin-4-ylamino)phenyl]2-(2-(diethylamino-3,4-dioxocyclobut-1-enylamino)propanoic acid;

and the salts, N-oxides and carboxylic acid esters thereof.

20. A compound according to claim 19 wherein the carboxylic acid esters are selected from the group consisting of methyl, ethyl, propyl, and i-propyl.

21. A pharmaceutical composition comprising a compound according to claim 1 together with one or more pharmaceutically acceptable carriers, excipients or diluents.

22. A method for the treatment of inflammatory arthritis, allograft rejection, diabetes, inflammatory dermatoses, asthma or inflammatory bowel disease comprising administering to a mammal suffering from such a disease or disorder a therapeutically effective amount of a compound according to claim 1.

23. A method according to claim 22 wherein said inflammatory arthritis is selected from the group consisting of rheumatoid arthritis, vasculitis and polydermatomyositis.

24. A method according to claim 22 wherein said inflammatory dermatoses are selected from the group consisting of psoriasis and dermatitis.

* * * * *